US011259739B2

(12) United States Patent
Daines

(10) Patent No.: US 11,259,739 B2
(45) Date of Patent: Mar. 1, 2022

(54) IMMUNOTHERAPY TREATMENT KIT AND METHOD OF USING THE SAME

(71) Applicant: PHD Preventative Health Care and Diagnostics, Inc., Colorado Springs, CO (US)

(72) Inventor: Eric R. Daines, Colorado Springs, CO (US)

(*) Notice: Subject to any disclaimer, the term of this patent is extended or adjusted under 35 U.S.C. 154(b) by 694 days.

(21) Appl. No.: 15/676,504

(22) Filed: Aug. 14, 2017

(65) Prior Publication Data

US 2018/0042545 A1 Feb. 15, 2018

Related U.S. Application Data

(60) Provisional application No. 62/374,345, filed on Aug. 12, 2016.

(51) Int. Cl.
| | | |
|---|---|---|
| *A61B 5/00* | (2006.01) | |
| *A61J 1/18* | (2006.01) | |
| *A61J 1/16* | (2006.01) | |
| *A61J 1/20* | (2006.01) | |

(52) U.S. Cl.
CPC ............. *A61B 5/411* (2013.01); *A61J 1/18* (2013.01); *A61J 1/165* (2013.01); *A61J 1/2089* (2013.01); *A61J 2205/10* (2013.01); *A61J 2205/20* (2013.01); *A61J 2205/60* (2013.01)

(58) Field of Classification Search
CPC ............. A61J 2205/60; A61J 2205/20; A61J 2205/10; A61J 3/00; A61J 3/074; A61J 1/2096; A61J 1/2089; A61J 1/165; A61J 1/16; A61J 1/1468; A61J 1/2003; A61J 1/20; A61J 1/18; A61L 35/411; A61L 35/41
See application file for complete search history.

(56) References Cited

U.S. PATENT DOCUMENTS

| | | | | |
|---|---|---|---|---|
| 2006/0286606 A1* | 12/2006 | Oliver | ................ | G01N 1/2214 435/7.1 |
| 2015/0231033 A1* | 8/2015 | Agren | ................ | B65D 25/108 206/568 |
| 2016/0368626 A1* | 12/2016 | Strader | ................ | A61K 39/35 |

FOREIGN PATENT DOCUMENTS

| | | | | |
|---|---|---|---|---|
| CN | 1852976 | * | 5/2012 | |
| WO | WO-2017044691 A | * | 3/2017 | ............. G16H 10/40 |

OTHER PUBLICATIONS

Nelson, et al. ("Allergen Immunotherapy Extract Preparation Manual", Chapter 9, AAAAI Practice Management Resource Guide, 2012 edition (Year: 2012).*

* cited by examiner

Primary Examiner — Matthew Kremer
Assistant Examiner — Avery M Foley
(74) Attorney, Agent, or Firm — Scott J. Hawranek

(57) ABSTRACT

The invention generally relates to medical kits, e.g., an immunotherapy treatment and testing kits, and more particularly to a method of using the kits and system for treating allergies.

13 Claims, 26 Drawing Sheets

IMMUNOTHERAPY TREATMENT KIT AND METHOD OF USING THE SAME

CROSS REFERENCE TO RELATED APPLICATION

This application claims the benefit under 35 U.S.C. § 119(e) of U.S. Provisional Application No. 62/374,345, filed Aug. 12, 2016, the content of which is fully incorporated by reference herein.

BACKGROUND OF THE INVENTION

Field of the Invention

The present invention generally relates to medical kits and methods of using the same, e.g., an immunotherapy treatment and testing kits, and more particularly to a kit and method of using for treating allergies.

SUMMARY OF THE INVENTION

Accordingly, the invention is directed to an immunotherapy treatment kit and method of using the same that substantially obviates one or more of the problems due to limitations and disadvantages of the related art.

An advantage of the invention is to provide a quick to use immunotherapy testing kit, immunotherapy mixing kit and immunotherapy patient therapy kit.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a system for testing an allergic response of a patient to one or more allergens including an immunotherapy testing kit comprising a container having a housing for holding one or more prefilled reservoirs containing one or more allergens, wherein the one or more prefilled reservoirs including a removable lid or stopper configured to substantially prevent or reduce spillage of the prefilled reservoirs during shipping and handling from a first location to a second location, wherein the lid or stopper comprises an elastomeric material, and one or more individual patient multiple skin test kits for puncture skin testing.

In another aspect and embodiment of the invention includes a system for preparing and mixing a custom immunotherapy treatment for a patient including one or more prefilled containers comprising an allergen extract determined by one or more information received by one or more of an allergy test, a clinician and a software program configured to programically deduce a patient specific diagnosis based on one or more inputs. The system also a container having a plurality of compartments for receiving the one or more prefilled containers and securely holding the one or more prefilled containers during shipping and handling and a refrigeration unit configured to keep the one or more prefilled containers within a predetermined temperature range for seventy two hours or less. Moreover, the system also includes one or more color coded vials used for mixing contents of the one or more prefilled containers.

Another aspect and embodiment of the invention includes a method for preparing and mixing a custom immunotherapy treatment for a patient providing an immunotherapy patient treatment. The method includes receiving an immunotherapy mixing kit, the immunotherapy mixing kit comprising a container, an immunotherapy patient packet, a sterile napkin, a patient prescription package, a clinic prescription package, and a first prefilled container with a first allergen extract, a second prefilled container with a second allergen extract, a third prefilled container with a third allergen extract, a fourth prefilled container with a fourth allergen extract, and a fifth prefilled container with a fifth allergen extract. In this embodiment, the patient prescription package includes an empty sterile vial with a color code indicative of a concentrate concentration, one or more needles, one or more rubber bands, and one or more alcohol wipes. In this embodiment, the clinic prescription package includes a first vial comprising a color code indicative of 1:5000 concentration, the first vial is prefilled with albumin buffered saline (ABS) dilute, a second vial comprising a color code indicative of 1:500 concentration the second vial is prefilled with albumin buffered saline (ABS) dilute, a third vial comprising a color code indicative of 1:50 concentration the third vial is prefilled with albumin buffered saline (ABS) dilute, a fourth vial comprising a color code indicative of 1:5 concentration the fourth vile is prefilled with albumin buffered saline (ABS) dilute, a fifth vial comprising a color code indicative of 1:5 concentration the fifth vial is prefilled with albumin buffered saline (ABS) dilute, and a sixth vial comprising a color code indicative of 1:5 concentration the sixth vial is prefilled with albumin buffered saline (ABS) dilute. The method also includes filling the concentrate vial with the contents of the first prefilled container, the second prefilled container, the third prefilled container, the fourth prefilled container, and the fifth prefilled container to form an allergen concentrate mix.

This Summary section is neither intended to be, nor should be, construed as being representative of the full extent and scope of the present disclosure. Additional benefits, features and embodiments of the present disclosure are set forth in the attached figures and in the description herein below, and as described by the claims. Accordingly, it should be understood that this Summary section may not contain all of the aspects and embodiments claimed herein.

Additionally, the disclosure herein is not meant to be limiting or restrictive in any manner. Moreover, the present disclosure is intended to provide an understanding to those of ordinary skill in the art of one or more representative embodiments supporting the claims. Thus, it is important that the claims be regarded as having a scope including constructions of various features of the present disclosure insofar as they do not depart from the scope of the methods and apparatuses consistent with the present disclosure (including the originally filed claims). Moreover, the present disclosure is intended to encompass and include obvious improvements and modifications of the present disclosure.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
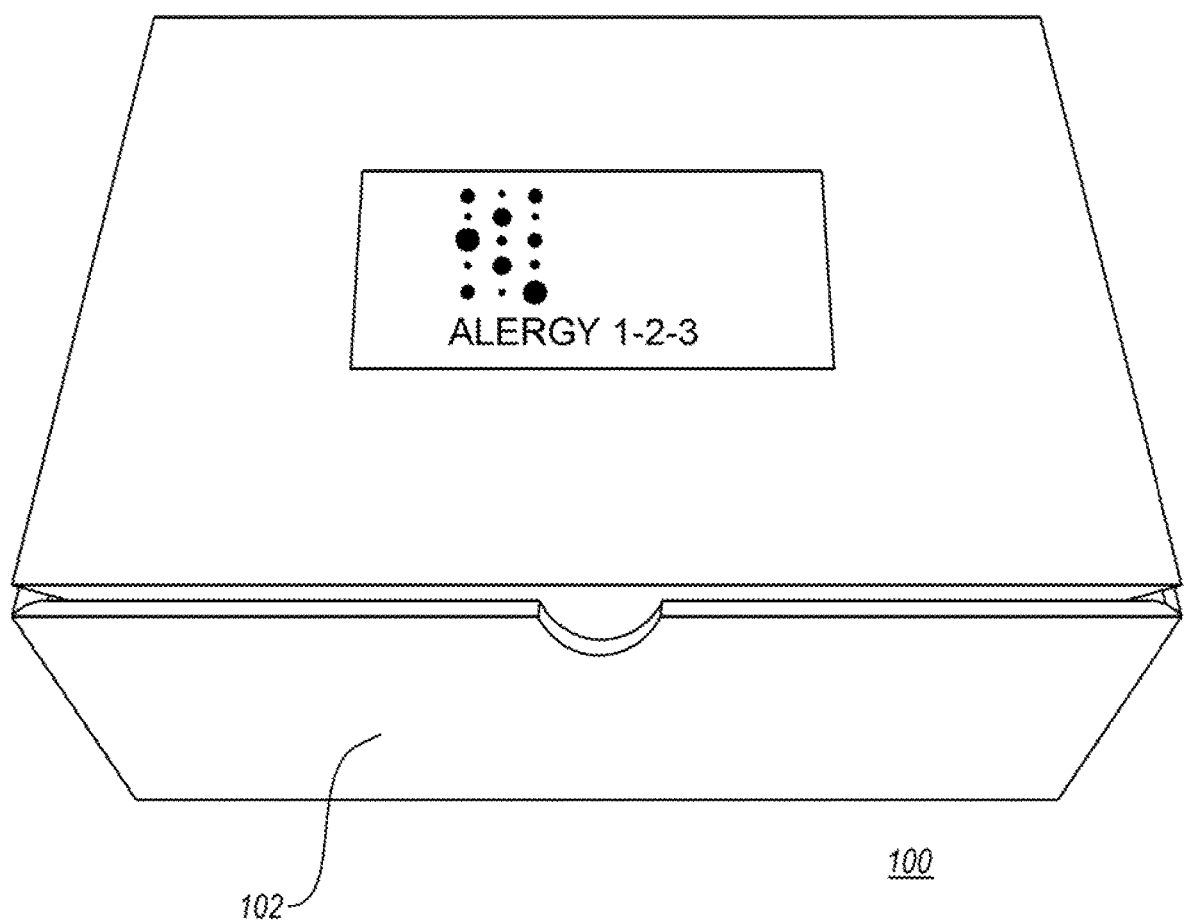
FIG. 1 illustrates an exemplary immunotherapy treatment kit or mixing kit according to an embodiment of the invention.

In order to more fully appreciate the present disclosure and to provide additional related features, the following references are incorporated therein by reference in their entirety:

(1) U.S. Pat. Application Publication No. 2016/0026765 by Daines, et al. which discloses, an immunotherapy system and method thereof, and more particularly to a method and system for providing, generating, tracking an immunotherapy treatment. The system further is directed towards a patient specific immunotherapy treatment recommendation at one or more devices that includes receiving, from one or more locations, a first input comprising information indicative of a patient medical history, a second input comprising information having characteristics indicative of one or more science factors, a third input comprising information having characteristics indicative of a patient's immune response to one or more antigens of a test; and generating, using a processor, an immunotherapy treatment recommendation based on the first input, the second input and the third input.

(2) U.S. Pat. Application Publication No. 2016/0022539 by Daines, et al. which discloses a prefilled disposable medication device, method of making, and using to the same, contain and deliver at least a diluent for allergenic extract and more particularly to a prefilled cartridge containing a diluent for allergenic extract for use with an injection pen for allergy treatments.

(3) U.S. Design Pat. No. D596758 by Constable, directed a spacer for an allergy testing kit.

One embodiment is direct towards a method for providing immunotherapy. In one embodiment, the allergy testing kit is configured to determine a patient's treatment for allergies in response to one or more of an immunotherapy test, a clinician and software configured to programically deduce a treatment. The allergy test kit is configured to be mailed to a provider's office and allows for ease of use by a minimally trained medical technician. The allergy testing kit includes multiple skin test devices for puncturing the skin and providing an extract to a patient to give an immune response, one or more test trays and one or more skin test reservoirs arranged in the one or more test trays containing one or more allergens, each skin test reservoir including a stopper or lid to cover the reservoir and substantially prevent the one more allergens from leaking or spilling during shipping or transport, optionally a spacer is arranged between the stopper or lid and one or more skin test reservoirs to avoid displacement of the stopper into the prefilled reservoirs.

The method includes testing a patient for an allergic response with the allergy testing kit and inputting results of test into an electronic device to provide a treatment recommendation for the patient and providing a prescription to a third-party based on the provided treatment recommendation. The electronic device software, method and steps to programically deduce the treatment recommendation is described with reference to U.S. Patent Application Publication 2016/0026765, which is hereby incorporated by reference as if fully set forth herein. The patient specific immunotherapy treatment system includes a network interface configured to receive a first input, second input and third input. A first input includes information having characteristics indicative of a patient's medical history, a second input includes information having characteristics indicative of one or more science factors, and a third input includes information having characteristics indicative of a patient's immune response to one or more antigens of a test. In this embodiment, the results for the third input are obtained with use of the allergy testing kit by a medical provider and patient. In one embodiment, the electronic device includes a processor on one or more of a server, patient device or provider device are configured to process the first input, the second input and the third input to determine an immunotherapy treatment recommendation.

Another embodiment is directed towards an immunotherapy mixing kit is configured to allow a provider to rapidly mix a custom immunotherapy for a patient. The custom immunotherapy includes increased concentrations based on a predetermined algorithm or mathematical function, e.g., a linear line with a positive slope, for a predetermined amount of time, e.g., a six week basis. In a preferred embodiment, the immunotherapy treatment after the mix includes administering two shots per week for six weeks at a first concentration, e.g., 5000 dilution for six weeks. The volume of each shot changes as a linear function, e.g., 0.03 mL increments. That is, the first shot, week one, concentration of 5000 dilution would be at a starting amount, e.g., in a range from about 0.02 mL to about 0.04. The second shot that week would be adjusted by about 0.03 mL with the same dilution amount. The maximum volume would be in week six and would not exceed 0.39 mL.

Moreover, the shots should be given at least 48 hours apart in each week. It is noted this would be considered a first round of treatment at the first concentration of allergen extract. The treatments may be provided by either a provider or a patient with an injection device. In addition, it is understood that this treatment may be adjusted based on adverse reactions from the patients. In one embodiment, the method is adjusted by a predetermined criteria by reducing the volume to one or more previously successfully administered treatment without adverse reactions.

By way of example, one embodiment is directed towards a six week treatment of increased dosage or volume also called a ramp over a predetermined time frame, which may be administered with a prefilled vials utilizing an injection device, e.g., automatic, needleless or needle. Optionally, a pretreatment prior to the treatment set is utilized in order to reduce adverse reactions, preferably, the pretreatment is configured as one injection at a dosage or volume configured to prevent any next increase from being higher than fifty percent. In preferred embodiment, the dosage or volume of the pretreatment is in a range from about 0.01 ml to about 0.04 ml, and more preferably about 0.04 ml.

Ramping a concentration of the treatment may be a predetermined time frame from about 1 week to 6 weeks or greater, preferably 6 weeks. In one ramping embodiment, a pretreatment injection of about 0.04 ml was administered with the injection device or other instrument and prefilled cartridge. Next, the ramp started at a 1:5000 dilution according to the following schedule could be used as follows: Week 1: shot 1—0.06 mL, 5000 dilution, shot 2—0.09 mL, 5000 dilution; Week 2: shot 1—0.12 mL, 5000 dilution, shot 2—0.15 mL, 5000 dilution; Week 3: shot 1—0.18 mL, 5000 dilution, shot 2—0.21 mL, 5000 dilution; Week 4: shot 1—0.24 mL, 5000 dilution, shot 2—0.27 mL, 5000 dilution; Week 5: shot 1—0.30 mL, 5000 dilution, shot 2—0.33 mL, 5000 dilution; Week 6: shot 1—0.36 mL, 5000 dilution, shot 2—0.39 mL, 5000 dilution. Next, the concentration is increased to a mixture with a concentration of 1:500 vol/vol or 500 dilution and a six week treatment set is repeated, however, the starting point is not 0.03 mL, but 0.06 mL, therefore the ending point in week six is 0.39 mL. This is repeated for the rest of the concentrations in six week increments until the 1.5 vol/vol or 5 dilution is given in the six week ramp treatment. Next a maintenance schedule is given for about six months or longer. The maintenance schedule is linear, and two shots per week at 0.30 mL to 0.39 mL are given. There is no change in volume from week to week or concentration from week to week or shot to shot. The amount of volume change between shots and durations of schedules is dependent on the efficacy and safety of the immunotherapy and may be adjusted to stay within the efficacy and safety bounds.

The term "allergen", "allergenic extract", "allergen extract", "extract", and "antigen" are used herein interchangeably. In one embodiment, the allergen extract is configured to elicit an immune response. Optionally, the allergen extract includes one or more of a tree pollen vector allergen, grass pollen vector allergen, weed pollen vector allergen, mold vector allergen and other vector allergen.

In one embodiment, the allergen in either the immunotherapy testing kit and/or immunotherapy treatment kit or mixing kit contains any substance that is configured to elicit an immune response. The extracts are used in an immunotherapy that is mixed with the mixing kit and the prefilled syringes containing the extracts include one more allergens also called an antigen configured to elicit an immune response. In a preferred embodiment, the allergens are classified into broad categories based on a transmission or other functional characteristics of the allergens. For example, the first category is called a vector group, and includes a pollen vector group, an animal vector group, a control vector group and an environment vector group.

In addition, these vector groups can have a further classification of allergens into sub-vector groups below each vector group. For example, the pollen vector group includes a tree sub-vector group, a grass sub-vector group, a weed sub-vector group, a plant sub-vector group and other pollen transmitting sub-vector groups. The animal vector group includes an indoor animal sub-vector group and an outdoor animal sub-vector group. The control vector group includes a saline control sub-vector group and histamine control sub-vector group. The environmental vector group includes a mold sub-vector group and cockroach allergens. Optionally and/or alternatively, the allergens within each sub-vector group may be further classified into one or more of seasons, amount of pollen produced per a predetermined time of one or more plant, tree, weed, or grass associated with each a specific vector group, sub-vector group or both, a cross-reactivity designation of one or more antigens in each sub-vector group, a frequency designation of one or more plant, tree, weed, or grass associated with each a specific vector group, sub-vector group or both per a predetermined area, and meteorological factors associated with one or more plant, tree, weed, or grass associated with each specific vector group, sub-vector group.

In one embodiment, the tree sub-vector group includes one or more allergens, e.g., an Acacia, Golden (*Acacia longifolia*); Alder, Red (*alnus rubra* (oregona)); Ash, White (*Faxinus grandifolia*); Beech, American (*Fagus grandifolia*); Birch Mix (Paper, River/Red & White Birch); Boxelder/Maple Mix (Boxelder, Hard Maple & Red Maple); Cedar, Mountain (*Jumperus ashei*); Cedar, Red (*Juniperus virginiana*); Cottonwood, Common (*Populus deltoides*); Cypress, Arizona (*Curpressus arizonica*); Cypress, Bald (*Taxodium distichum*); Elm, American (*Ulmus americana*); Elm, Chinese (*Ulmus parvifolia*); Eucalyptus/Blue Gum (*Eucalyptus globulus*); Gum, Sweet (*Liquidambar styraci-*

*flua*); Hackberry (*Celtis occidentalis*); Hickory, Shagbark (*Carya ovata*); Linden/Basswood (*Tilia americana*); Maple, Hard/Sugar (*Acer saccharum*); Mesquite (*Prosopis juliflora* (glandulosa)); Mulberry Mix (Red & White Mulberry); Oak, Red (*Quercus rubra*); Oak Mix (Red, Virginia Live & White Oak); Olive Tree (*Olea europaea*); Bottlebrush Tree (*Callistemon citrinus*); Melaleuca (*Melaleuca quinquenervia*); Palm, Queen (Cocos plumose); Pecan Tree (*Carya pecan* (illinoensis)); Pepper Tree, California (*Schinus molle*); Pine Mix (Lodgepole & Western Yellow Pine); Privet, Common (*Lingustrum vulgare*); Russian Olive (*Elaeagnus angustifolia*); Sycamore, American (*Platanus occidentalis*); Tree Mix (Pecan, Maple, Oak, American Sycamore, Black Willow); Tree Mix (White Ash, American Beech, Birch, Black Walnut, Common Cottonwood, American Elm); Tree Mix (White Ash, American Beech, River/Red Birch, Black Walnut, Common Cottonwood, American Elm, Shagbark Hickory, Hard Maple, Red Oak, American Sycamore, Black Willow); Walnut, Black (*Juglans nigra*); Willow, Black (*Salix nigra*); and the like.

There are a number of different allergens configured in the grass sub-vector group. In one embodiment, the allergens in this grass sub-vector group include one or more of Acacia, Bahia Grass (*Paspalum notatum*); Bermuda Grass (*Cynodon dactylon*); Bluegrass, Kentucky (*Poa pratensis*); Brome, Smooth (*Bromus inermis*); Corn, Cultivated (*Zea mays*); Fescue, Meadow (*Festuca elation* (pratensis)); Grass Mix (Kentucky Bluegrass, Orchard, Redtop, Timothy); Grass Mix (Kentucky Bluegrass, Orchard, Redtop, Timothy, Sweet Vernalgrass); Grass Mix (Kentucky Bluegrass, Orchard, Redtop, Timothy, Sweet Vernalgrass, Meadow Fescue, Perennial Ryegrass); Grass Mix (Kentucky Bluegrass, Bermuda, Johnson, Redtop, Timothy); Johnson Grass (*Sorghum halepense*); Oats, Common Cultivated (*Avena sativa*); Orchard Grass (*Dactylis glomerate*); Redtop (*Agrostis gigantea* (alba)); Ryegrass, Perennial (*Lolium perenne*); Southern Grass Mix (Kentucky Bluegrass, Orchard, Redtop, Timothy, Sweet Vernalgrass, Bermuda, Johnson); Sweet Vernalgrass (*Anthoxanthum odoratum*); Timothy (*Phleum pratense*); and the like.

There are a number of different allergens configured in the weed sub-vector group. In one embodiment, the allergens the weed sub-vector group include one or more of Acacia, Careless Weed (*Amaranthus palmeri*); Careless/Pigweed (Careless Weed & Rough Redroot Pigweed); Cocklebur, Common (*Xanthium strumarium*); Dock/Sorrel Mix (Yellow Dock & Sheep Sorrel); Goldenrod (*Solidago canadensis*); Kochia (*Kochia scoparia*); Lamb's Quarters (*Chenopodium album*); Marshelder/Poverty Mix (Burwee, Povertyweed & True Marshelder); Nettle (*Urtica dioica*); Dog Fennel, Eastern (*Eupatorium capillifolium*); Pigweed, Rough Redroot (*Amaranthus retroflexus*); Plantain, English (*Plantago lanceolata*); Ragweed, Giant (*Ambrosia trifida*); Ragweed, Short (*Ambrosia artemisilifolia*); Ragweed, Western (*Ambrosia psilostachya*); Ragweed Mix (Giant & Short Ragweed); Ragweed (Giant, Short & Western Ragweed); Russian Thistle (*Salsola kali*); Sagebrush, Mugwort (*Artemisia vulgaris Heterophylla* (douglasiana)); Scale, Wing (*Atriplex canescens*); Sheep Sorrel (*Rumex acetosella*); Weed Mix 2630 (Common Cocklebur, Lamb's Quarters, Rough Redroot Pigweed, Dock/Sorrel); and the like.

There are a number of different allergens configured in the mold sub-vector group. In one embodiment, the allergens the mold sub-vector group include one or more of *Alternaria-Hormodendrum* Mix (*Alternaria tenuis, Hormodendrum cladosporioides*) *Alternaria tenuis; Aspergillus fumigatus; Aspergillus niger; Botrytis cinerea; Candida albicans; Cephalosporium acremonium; Curvularia spicifera; Epicoccum nigrum; Epidermophyton floccosum; Fusarium vasinfectum; Helminthosporium interseminatum; Hormodendrum cladosporioides; Mucor racemosus; Penicillium* Mix (*p. digitatum, expansum, glaucum, roseum, notatum*); *Penicillium notatum; Phoma herbarum; Pullularia pullulans; Rhizopus nigricans; Stemphylium botryosum; Trichopyton* Mix (*T. tonsurans, rubrum, mentagrophytes*); Mold Mix (*Alternaria tenuis, Aspergillus* Mix (*A. fumigatus, nidulans, niger, terreus*), *Hormodendrum cladosporioides, Penicillium* Mix (*P. digitatum, expansum, glaucum, notatum, roseum*); Mold Mix *Alternaria tenuis, Aspergillus* Mix (*A. fumigatus, nidulans, niger, terreus*), *Fusarium vasinfectum, Helminthosporium interseminatum, Hormodendrum cladosporioides, Mucor racemosus, Penicillium* Mix (*P. digitatum, expansum, glaucum, notatum, roseum*), *Phoma herbarum, Pullularia pullulans, Rhizopus nigricans*; and the like.

There are a number of different allergens configured in the animal vector group. In one embodiment, the allergens in this animal vector includes one or more of Dog Hair and Dander (Mixed breeds); Feather Mix (Chicken, Duck and Goose); Guinea Pig Hair and Dander; Cat Pelt; Cat Hair; Cattle Hair and Dander; Horse Hair and Dander; House Dust Mix (Feather and Mattress dust), DP Mite and DF Mite (even though not an animal); and the like.

There are a number of different allergens configured in the mold sub-vector group. In one embodiment, the allergens in this mold sub-vector group includes one or more of *Alternaria tenuis; Aspergillus fumigatus; Aspergillus niger; Candida albicans; Cephalosporium acremonium; Curvularia spicifera; Epidermophyton floccosum; Fusarium vasinfectum; Mucor racemosus; Hormodendrum; Helminthosporum; Penicillium* Mix; *Phoma herbarum; Pullularia pullulans; Rhizopus nigricans; Stemphylium botryosum; Trichopylton* Mix; *Epicoccum nigrum; Botrytis cinerea*, cockroach mix (even though not a mold), and the like.

In one embodiment, a diluent includes one or more of glycerin, Phenol, saline, and acrylonitrile butadiene styrene (ABS). In another embodiment, the diluent can include 0.9% NaCl, 0.03% human albumin, and 0.4% phenol in water. In yet another embodiment, the diluent can include about 50% glycerin and phenol. In still yet another embodiment, the diluent includes 0.4% phenol and/or saline. In yet another embodiment, the diluent includes 0.03% HSA, 0.4% phenol, and saline. In a preferred embodiment, the diluent includes only ABS with no other additives.

Reference will now be made in detail to an embodiment of the present invention, example of which is illustrated in the accompanying drawings.

Figure 2:
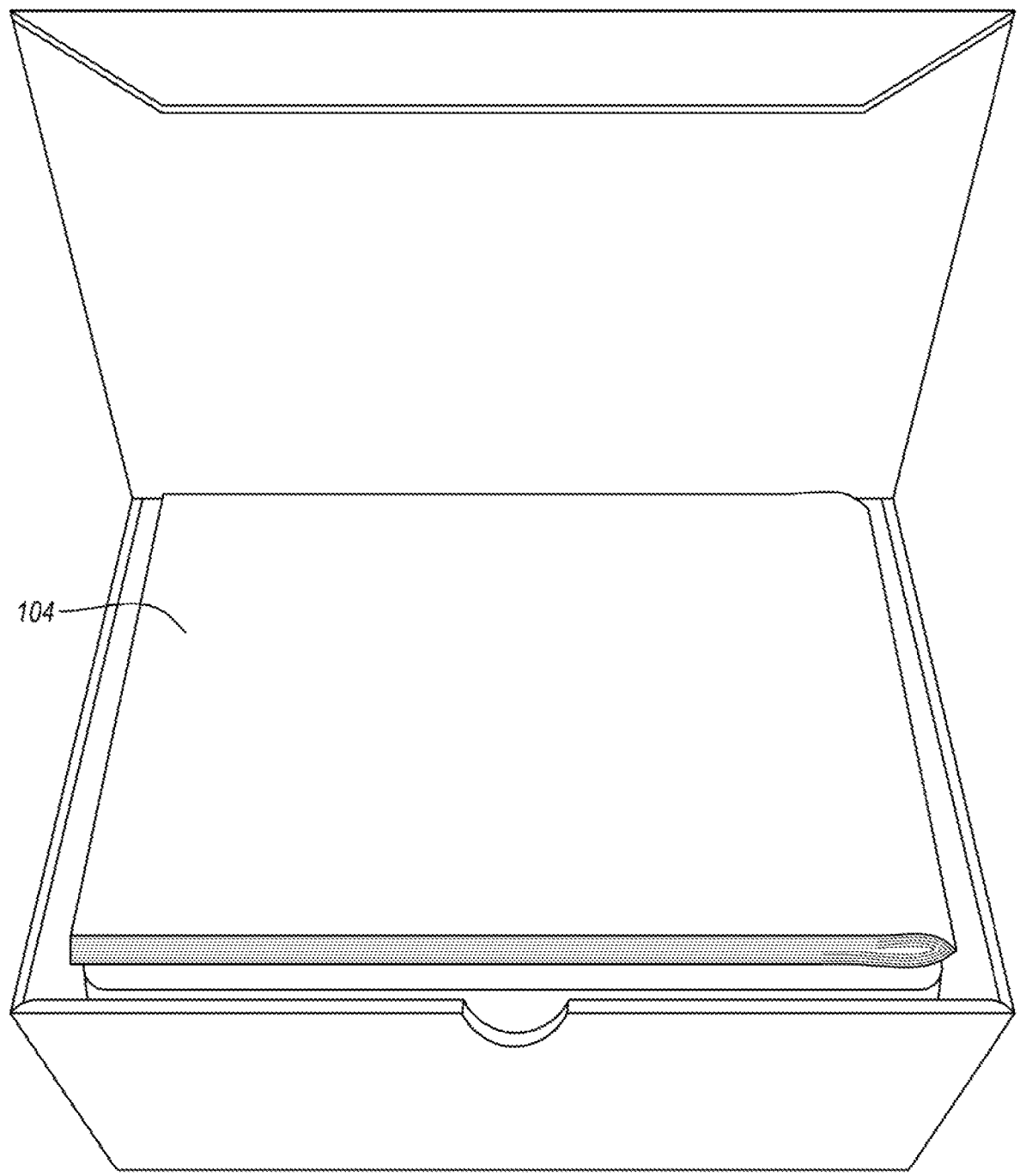
FIG. 2 illustrates the immunotherapy treatment kit according to FIG. 1.
Figure 3:
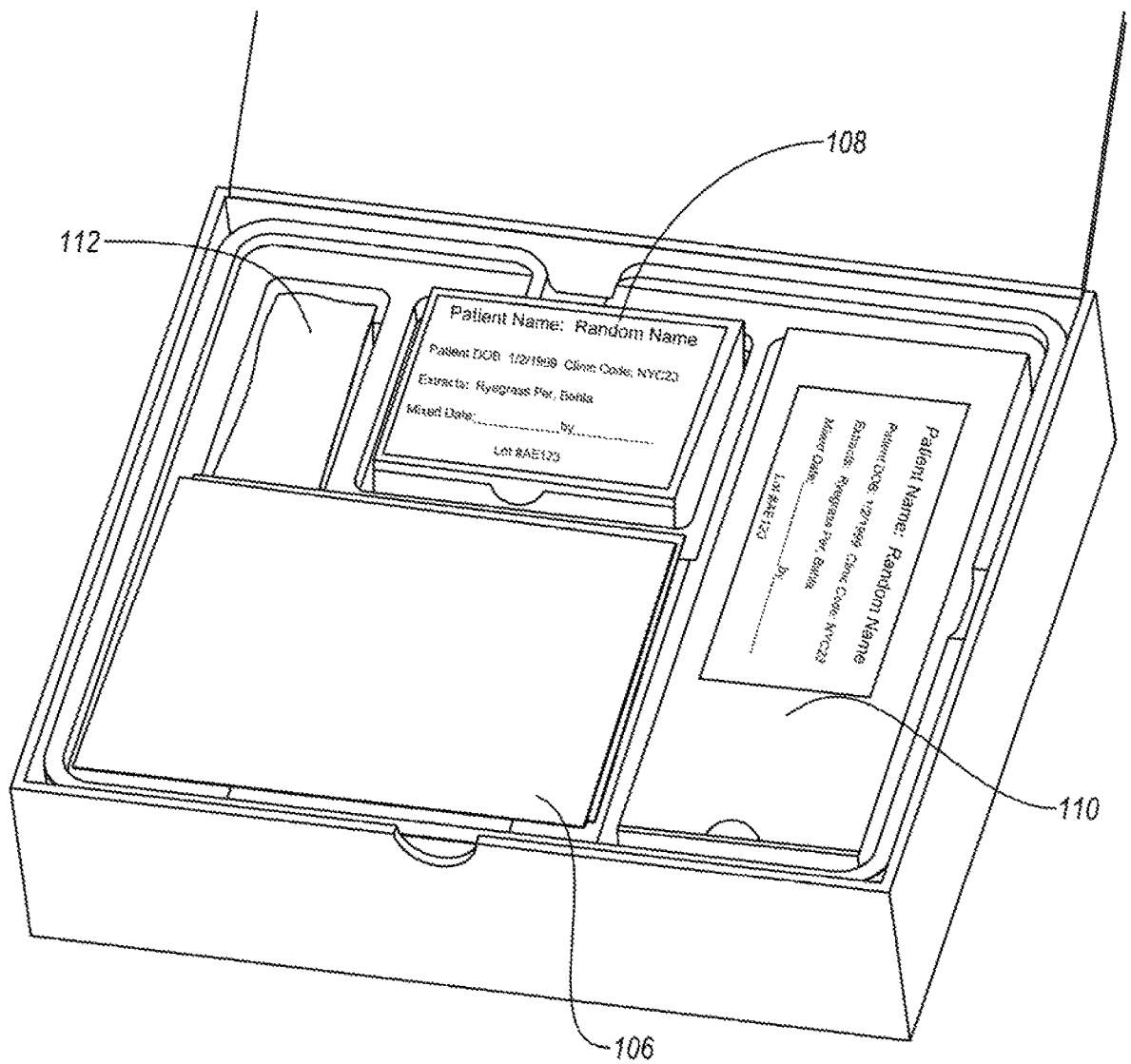
FIG. 3 illustrates the immunotherapy treatment kit according to FIG. 1.
Figure 4:
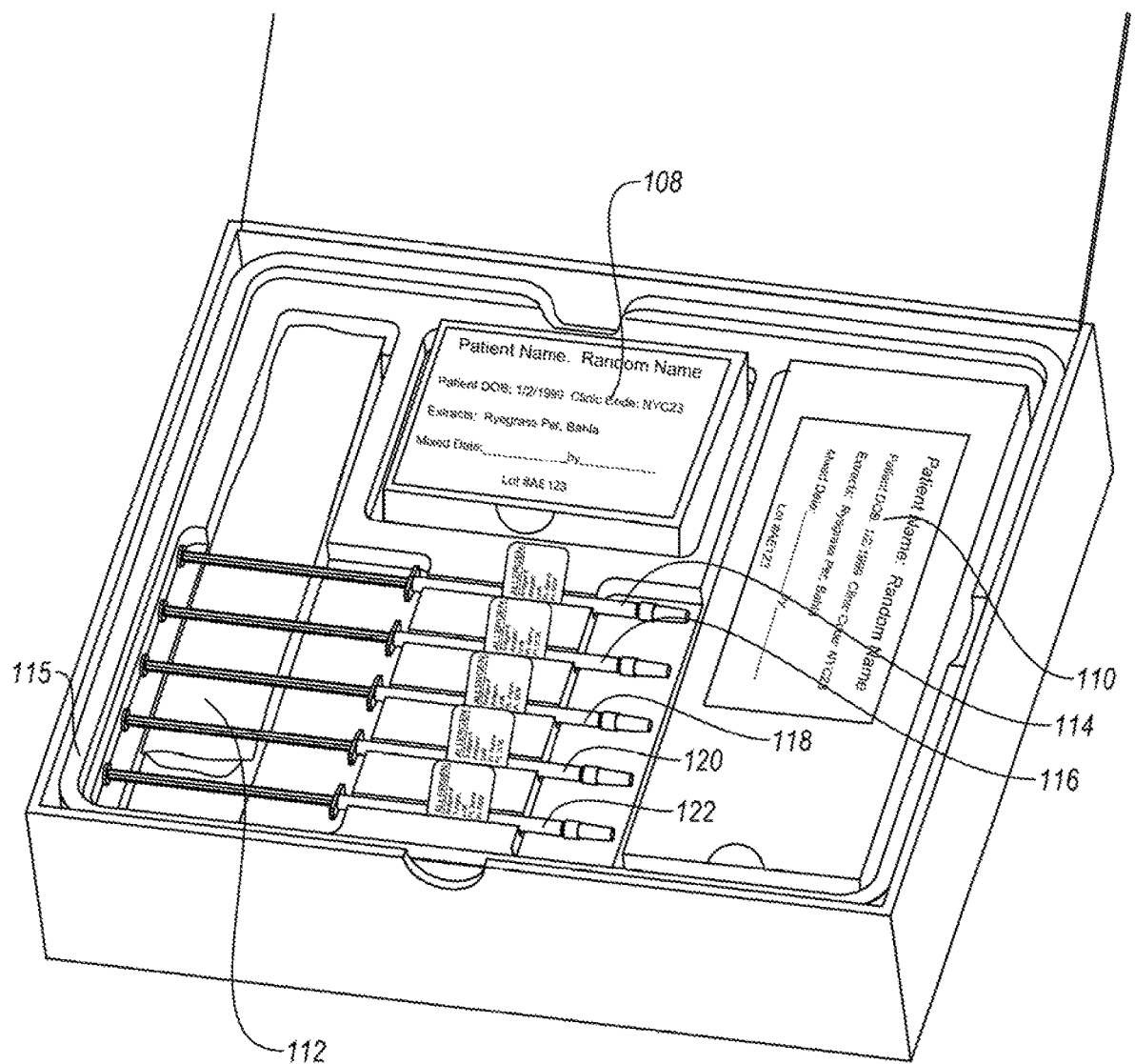
FIG. 4 illustrates the immunotherapy treatment kit according to FIG. 1.

FIG. 1 illustrates an exemplary immunotherapy treatment kit or mixing kit according to an embodiment of the invention. FIG. 2 illustrates the immunotherapy treatment kit according to FIG. 1. FIG. 3 illustrates the immunotherapy treatment kit according to FIG. 1. FIG. 4 illustrates the immunotherapy treatment kit according to FIG. 1.

Referring to FIGS. 1-4, the immunotherapy treatment kit is generally depicted as reference number 100. The immunotherapy treatment kit 100 includes a container 102. The container 102 is a cardboard box container configured to hold and transport the immunotherapy kit. Optionally, the container 102 may include any type of material, e.g., plastic, thermoplastic, cardboard, paper, and combination of the same. The kit 100 includes a immunotherapy patient packet 104, a sterile napkin 106, patient prescription package 108, clinic prescription package 110, mixing syringes 112, a first—1 cc prefilled syringe 114 with a first allergen extract for mixing a patient treatment prescription, a second—1 cc prefilled syringe 116 with a second allergen extract for mixing a patient treatment prescription, a third—1 cc prefilled syringe 118 with a third allergen extract for mixing a patient treatment prescription, a fourth—1 cc prefilled syringe 120 with a fourth allergen extract for mixing a patient treatment prescription, and a fifth—1 cc prefilled syringe 122 with a fifth allergen extract for mixing a patient treatment prescription. The type of allergen patient treatment prescription is custom immunotherapy treatment based on a patient's immune response. In a preferred embodiment, the type of patient treatment prescription extracts is generated with diagnostic software and/or hardware as described with reference to U.S. Patent Application Publication 2016/0026765, which is hereby incorporated by reference. Optionally and/or alternatively, the kit includes an electronic device, e.g., mobile device, computer, tablet or the like, configured to operate the diagnostic software.

Each of the items of the kit 100 are arranged in a preconfigured compartments in a thermo-mold 115. The thermo-mold 115 is configured to stay within a predefined temperature for keeping syringes below a predetermined temperature, e.g., in a preferred embodiment in a temperature range of about 32 degrees, above freezing, to about 46 degrees.

Figure 5:
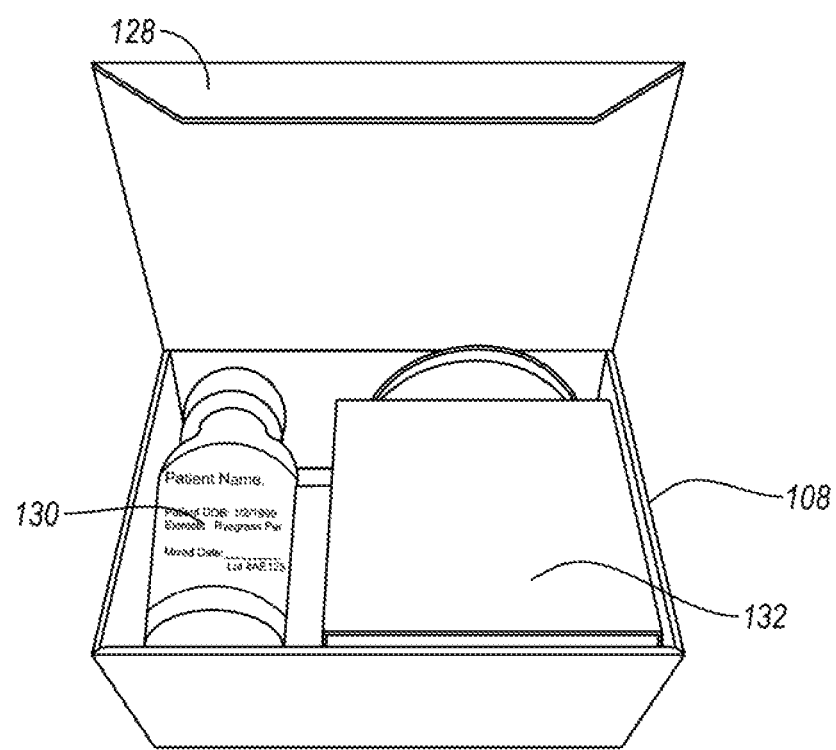
FIG. 5 illustrates the patient prescription package of the immunotherapy kit according to FIG. 1.
Figure 6:
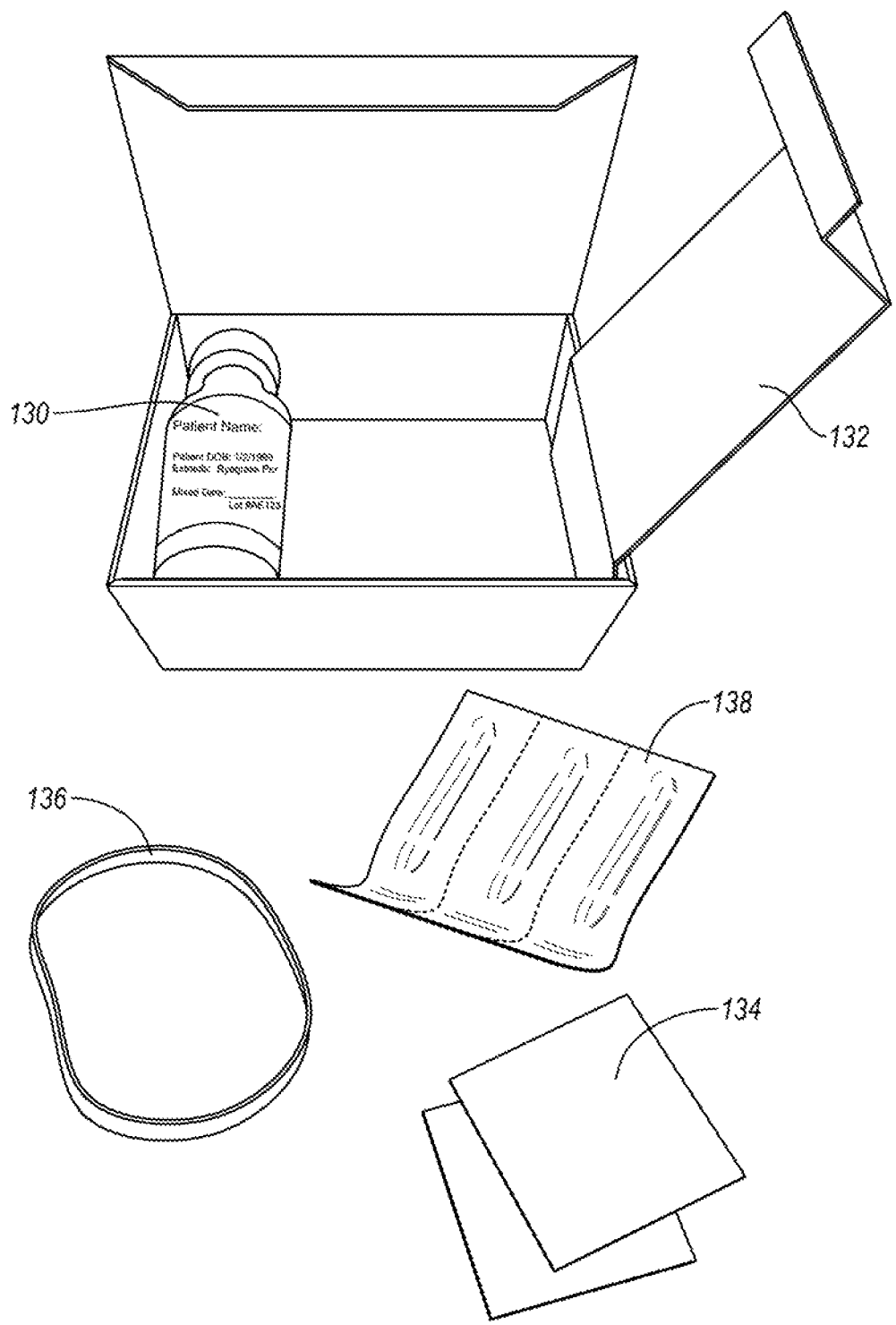
FIG. 6 illustrates the contents of a patient prescription package according to FIG. 5.
Figure 7:
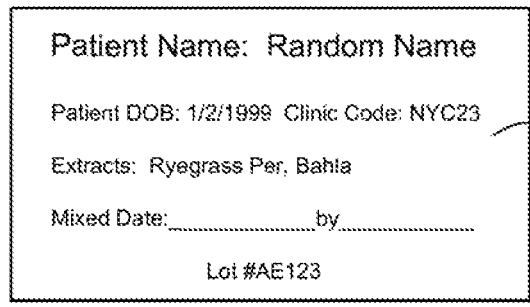
FIG. 7 illustrates the patient prescription package according to FIG. 5.

FIG. 5 illustrates the patient prescription package of the immunotherapy kit to FIG. 1. FIG. 6 illustrates the contents of the patient prescription according to FIG. 5. FIG. 7 illustrates the patient prescription package according to FIG. 5.

Referring to FIGS. 5-7, the patient prescription package 108 is configured to supply items necessary to mix immunotherapy at a clinic and can be used by the patient for home based immunotherapy. Referring to the patient prescription package 108 including a cardboard box configured from an open position to a closed position a top of the box 128, a flap 132 covering components of the package and a vial 130. Optionally, the box 128 may include any type of material, e.g., plastic, thermoplastic, cardboard, paper, and combination of the same. The vial 130 is a concentrate vial that is empty. Needles 138, alcohol wipes 134 and a rubber band 136. The patient prescription package 108 includes a label having information indicative of one or more of identity of a patient, identity of clinic, date of use, extracts being treated, mixing date, lot identification and refrigeration required label.

Figure 8:
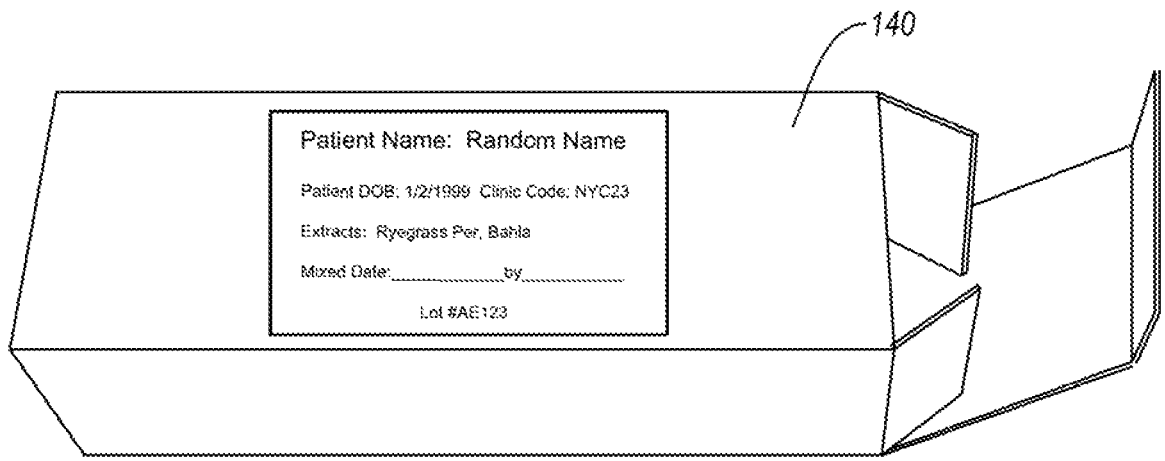
FIG. 8 illustrates the clinic prescription package of the immunotherapy kit according to FIG. 1.
Figure 8:
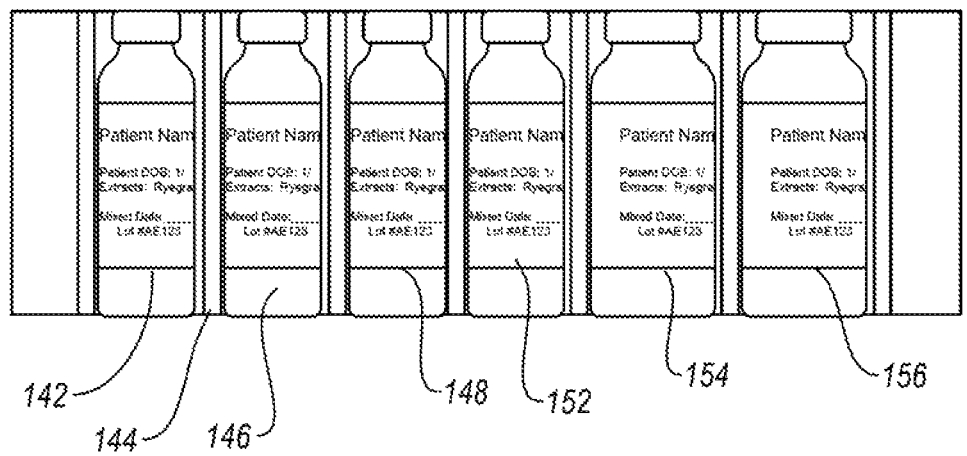

FIG. 8 illustrates the clinic prescription package of the immunotherapy kit to FIG. 1.

Referring to FIG. 8, clinic prescription package of the immunotherapy generally depicted as reference 140. The clinic prescription package is configured to be used with the patient package for mixing. The kit includes prefilled mixing containers to allow a clinician to mix the custom immunotherapy. The prefilled containers include dilute for immunotherapy. In a preferred embodiment the prefilled container are filed with ABS dilute.

Optionally and/or alternatively, the containers are color coded in order to indicate concentration of final immunotherapy, a container 142 includes a silver code on a cap portion indicative of 1:5000 concentration the container is 5 [cc] and prefilled with 4.5 [cc] of albumin buffered saline (ABS) dilute, a divider 144 is arranged between each container to avoid damage during shipping, container 146 includes a green code on a cap portion indicative of 1:500 concentration the container is 5 [cc] and prefilled with 4.5 [cc] of ABS dilute, container 148 includes a blue code on a cap portion indicative of 1:50 concentration the container is 5 [cc] and prefilled with 4.5 [cc] of ABS dilute, container 152 includes a yellow code on a cap portion indicative of 1:5 concentration the container is 5 [cc] and prefilled with 4.5 [cc] of ABS dilute, container 154 includes a yellow code on a cap portion indicative of 1:5 concentration the container is 10 [cc] and prefilled with 8 [cc] of ABS dilute, and container 156 includes a yellow code on a cap portion indicative of 1:5 concentration the container is 10 [cc] and prefilled with 8 [cc] of ABS dilute. Each container includes a label having information indicative of one or more of identity of a patient, identity of clinic, date of use, extracts being treated, mixing date, lot identification and refrigeration required label. Optionally, the containers do not need to be prefilled with ABS. In a preferred embodiment, the container includes a sterile capped container with a resalable portion to receive a needle. The container can be glass, thermoplastic or other material.

Figure 9:
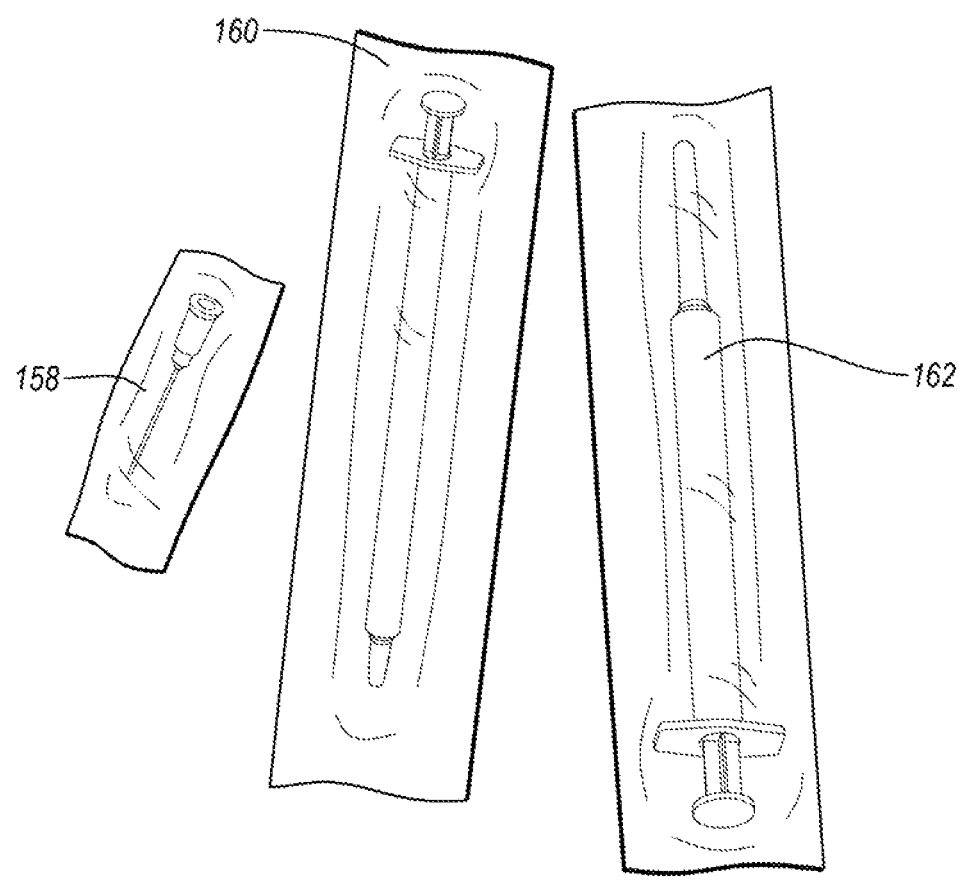
FIG. 9 illustrates mixing syringes of the immunotherapy treatment kit of FIG. 8.
Figure 10:
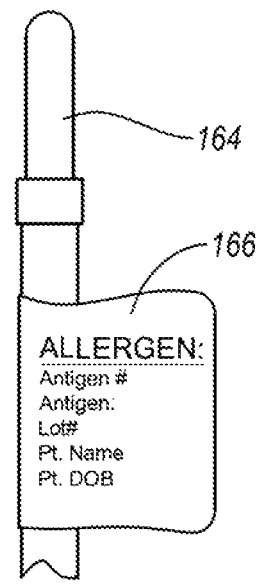
FIG. 10 illustrates a prefilled allergen extract syringe for mixing patient treatment of the immunotherapy treatment kit.
Figure 11:
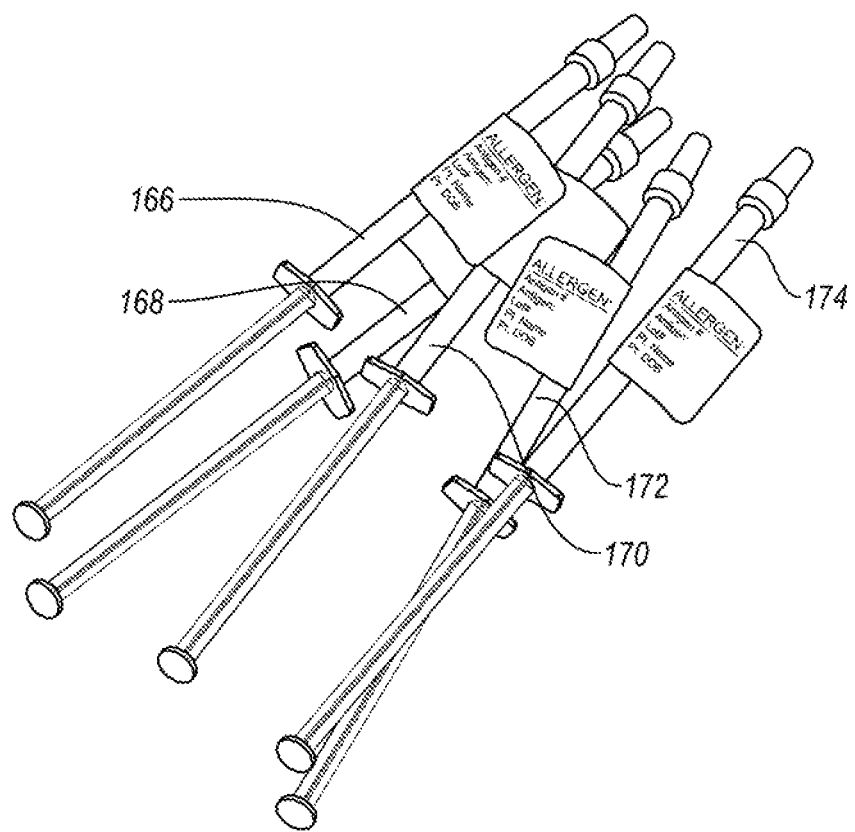
FIG. 11 illustrates five prefilled allergen extract syringes for mixing patient treatment of the immunotherapy treatment kit.

FIG. 9 illustrates mixing syringes of the immunotherapy treatment kit of FIG. 8. Referring to FIGS. 9-11, the mixing syringes include a plurality of syringes for example a 3 cc mixing syringe 162, a 1 cc mixing syringe 160, and a needle 158. Other components may be included to aid with mixing extracts.

FIG. 10 illustrates a close up view of 1 cc prefilled allergen extract syringe for mixing patient treatment of the immunotherapy treatment kit. FIG. 11 illustrates five 1 cc prefilled allergen extract syringes for mixing patient treatment of the immunotherapy treatment kit.

Referring to FIGS. 10-11, the kit includes 5 prefilled custom syringes with allergen extract. The contents of the prefilled custom syringes are determined by a medical professional in response to an allergy treatment test. Optionally and/or alternatively, the contents are determined with software and/or hardware and/or a medical professional as described with reference to U.S. Patent Application Publication 2016/0026765, which is hereby incorporated by reference. Optionally and/or alternatively there may be more than one extract or less than one extract in the prefilled custom syringes. In addition, there may be more than 5 prefilled syringes or less than 5 prefilled syringes.

The syringe 166 includes a cap 164 and is prefilled with a first allergen extract, syringe 168 includes a cap and is prefilled with a second allergen extract, syringe 170 includes a cap and is prefilled with a third allergen extract, syringe 172 includes a cap and is prefilled with a fourth allergen extract, and syringe 174 includes a cap and is prefilled with a fifth allergen extract. In a preferred embodiment, the cap includes a luer-lock cap. Optionally and/or alternatively as shown each syringe includes a label having information indicative of one or more of identity of a patient, identity of clinic, date of use, extract included, mixing date, lot identification and refrigeration required label. Optionally, the containers do not need to be prefilled with ABS.

Figure 12:
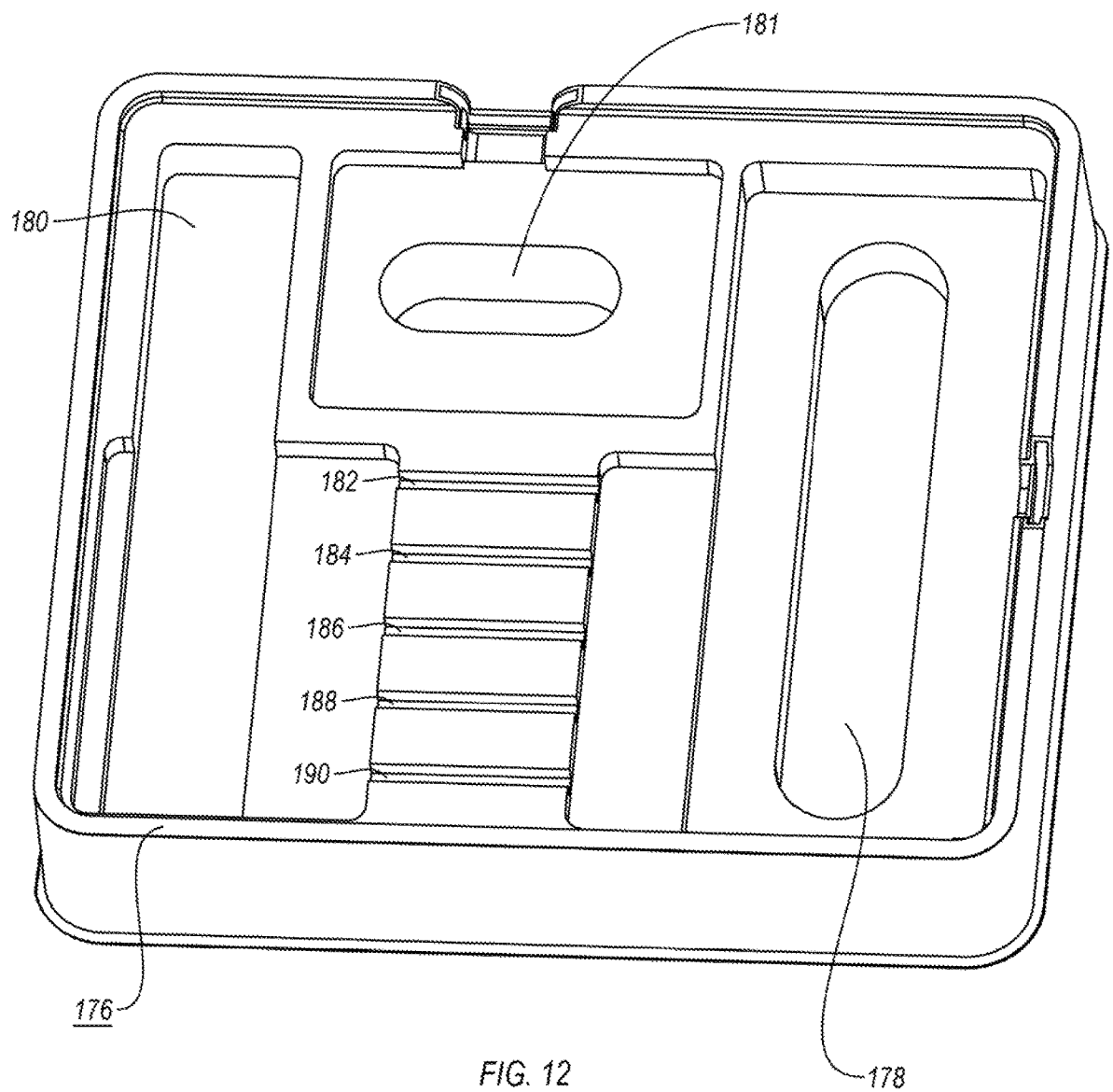
FIG. 12 illustrates a top side view of a thermoform of the immunotherapy treatment kit of FIG. 1.
Figure 13:
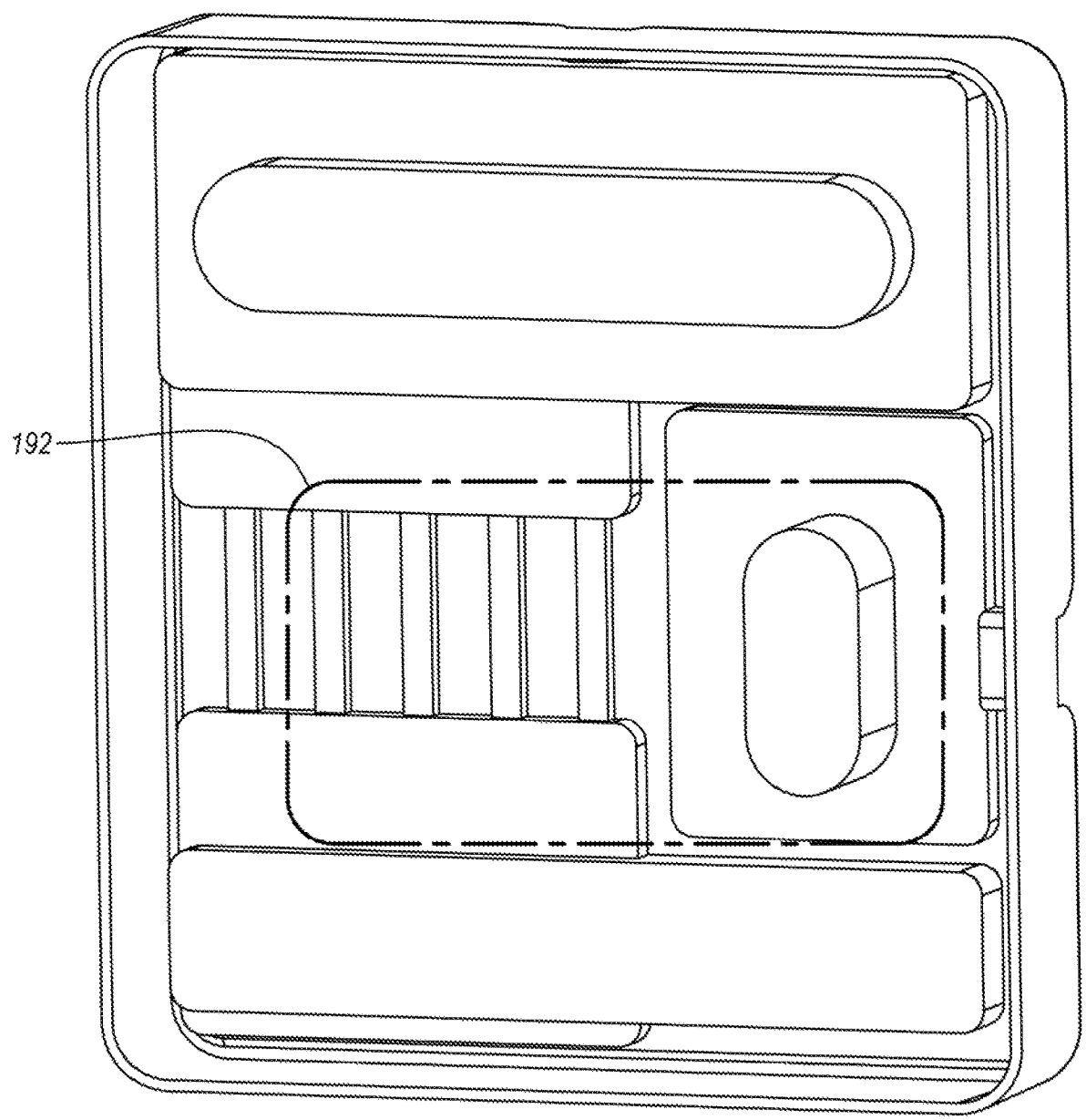
FIG. 13 illustrates a bottom side view of a thermoform of the immunotherapy treatment kit of FIG. 1.
Figure 14:
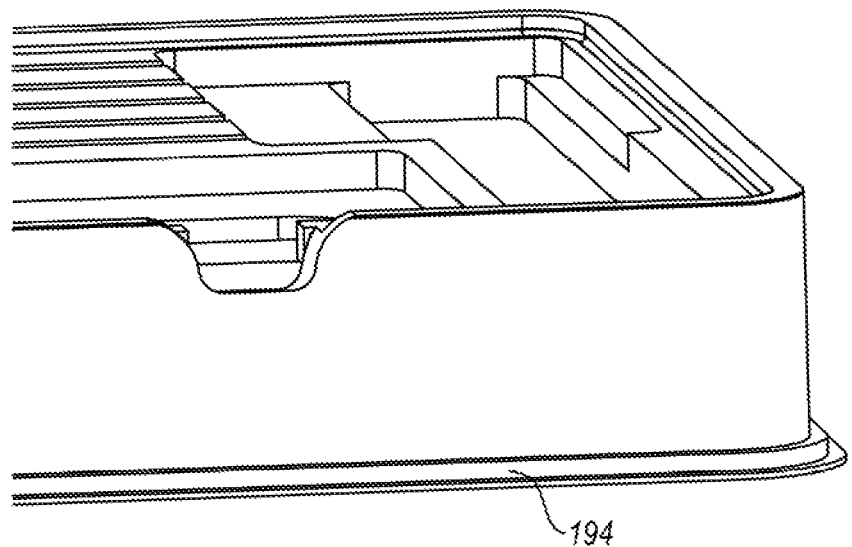
FIG. 14 illustrates a first side view of a thermoform of the immunotherapy treatment kit of FIG. 1.
Figure 15:
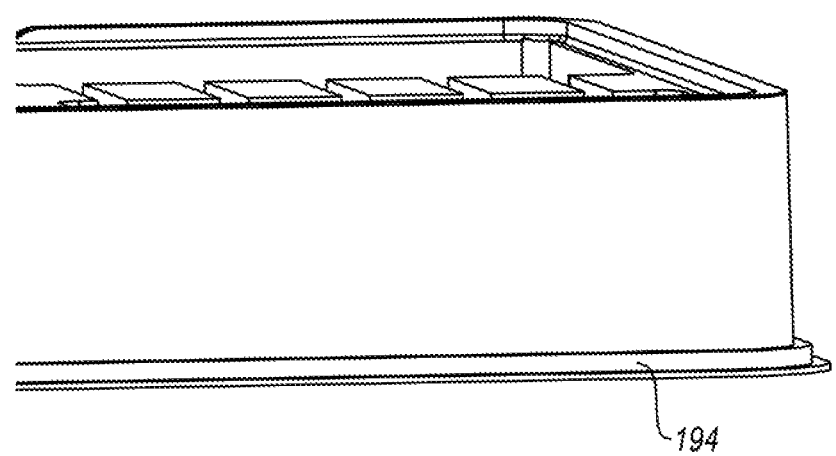
FIG. 15 illustrate a second side view of a thermoform of the immunotherapy treatment kit of FIG. 1.
Figure 16:
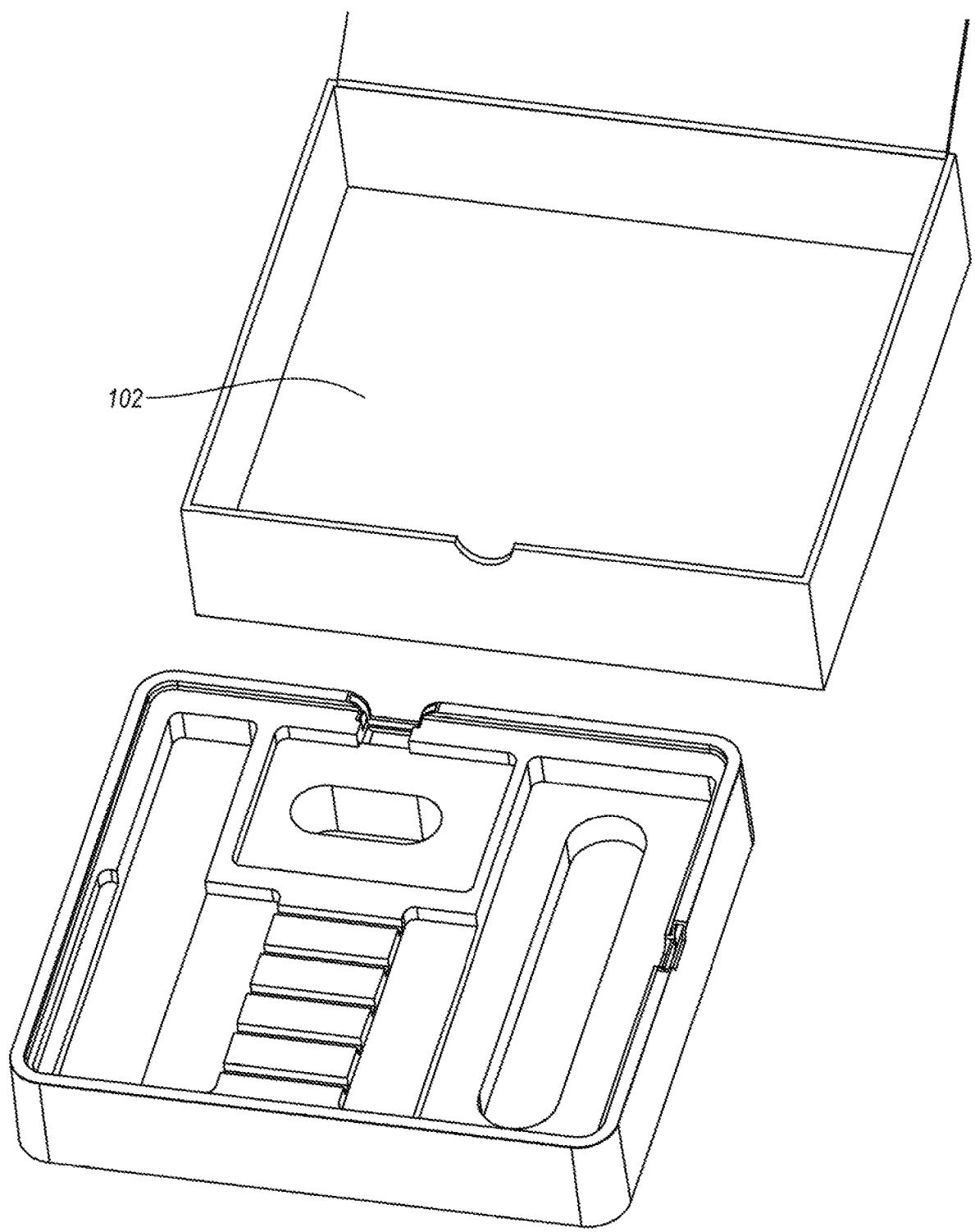
FIG. 16 illustrates a perspective view of a thermoform of the immunotherapy treatment kit of FIG. 1.

FIG. 12 illustrates a top side view of a thermoform of the immunotherapy treatment kit of FIG. 1. FIG. 13 illustrates a bottom side view of a thermoform of the immunotherapy treatment kit of FIG. 1. FIG. 14 illustrates a first side view of a thermoform of the immunotherapy treatment kit of FIG. 1. FIG. 15 illustrating a second side view of a thermoform of the immunotherapy treatment kit of FIG. 1. FIG. 16 illustrating a perspective view of a thermoform of the immunotherapy treatment kit of FIG. 1.

Referring to FIGS. 12-16, the thermoform is generally depicted with reference to number 176 and configured to substantially secure and retain components of the immunotherapy kit during shipping. The thermoform is fitted with a chamber 192 configured to receive an ice pack or other cooling device, e.g., dry ice, electric cooler, and the like, to keep prefilled syringes 166, 168, 170, 172 and 174 refrigerated for up to 72 hours. Optionally and/or alternatively, other types of refrigeration units may be used, e.g., sleeves around each syringe, electronic, and combinations of the same. The thermoform 176 includes a slot 178 for receiving a clinic prescription package 140, a slot 180 for receiving mixing syringes 158, 160, and 162, a slot 181 for receiving a patient prescription package 108, a slot 182 for receiving syringe 166, a slot 184 for receiving a syringe 168, a slot 186 for receiving a syringe 170, a slot 188 for receiving a syringe 172, and slot 190 for receiving a syringe 174. Optionally and/or alternatively the thermoform 176 includes a spacer 194 around a circumference of the thermoform 176, the spacer 194 is configured to substantially prevent movement in the container 102 in an x-y axis direction. The thermoform 176 is also sized vertically to prevent movement in the container in a z-axis direction.

Figure 17:
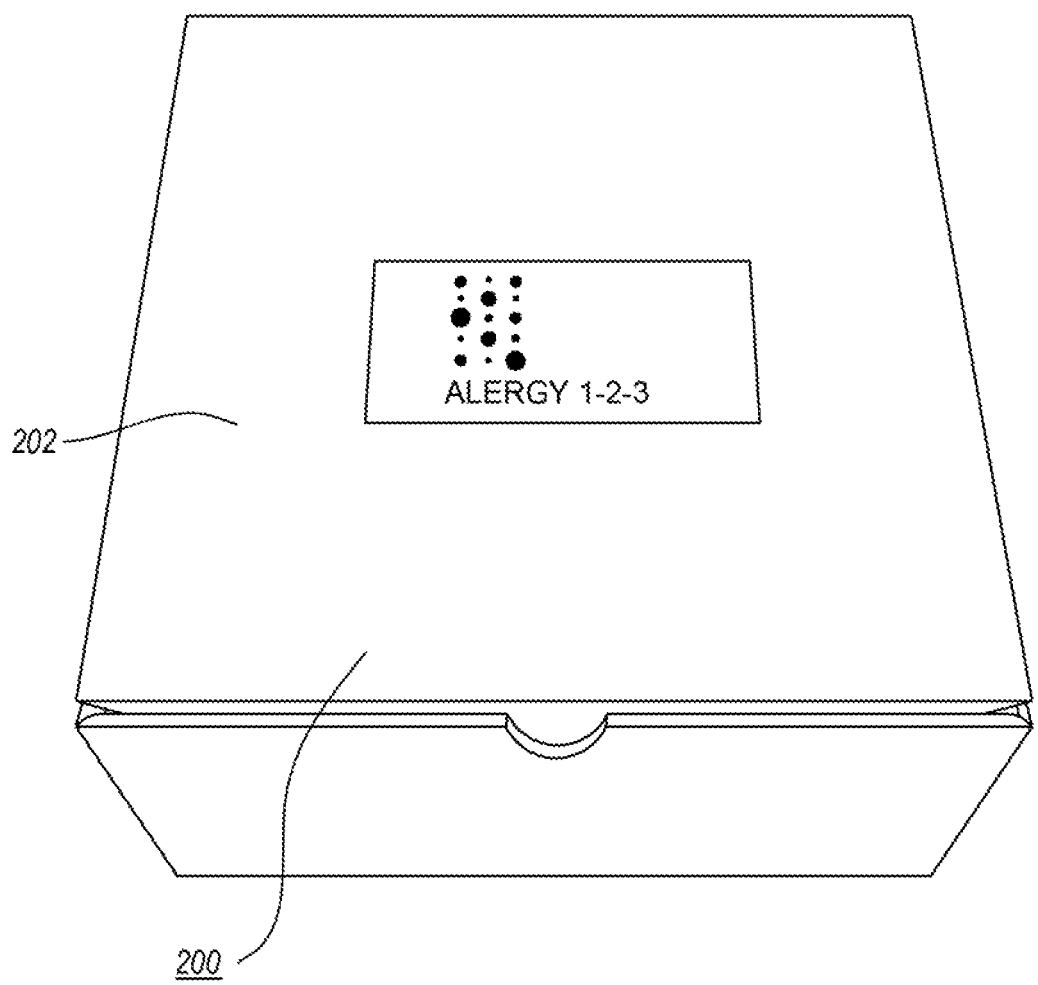
FIG. 17 illustrates an allergy testing kit according to an embodiment of the invention.
Figure 18:
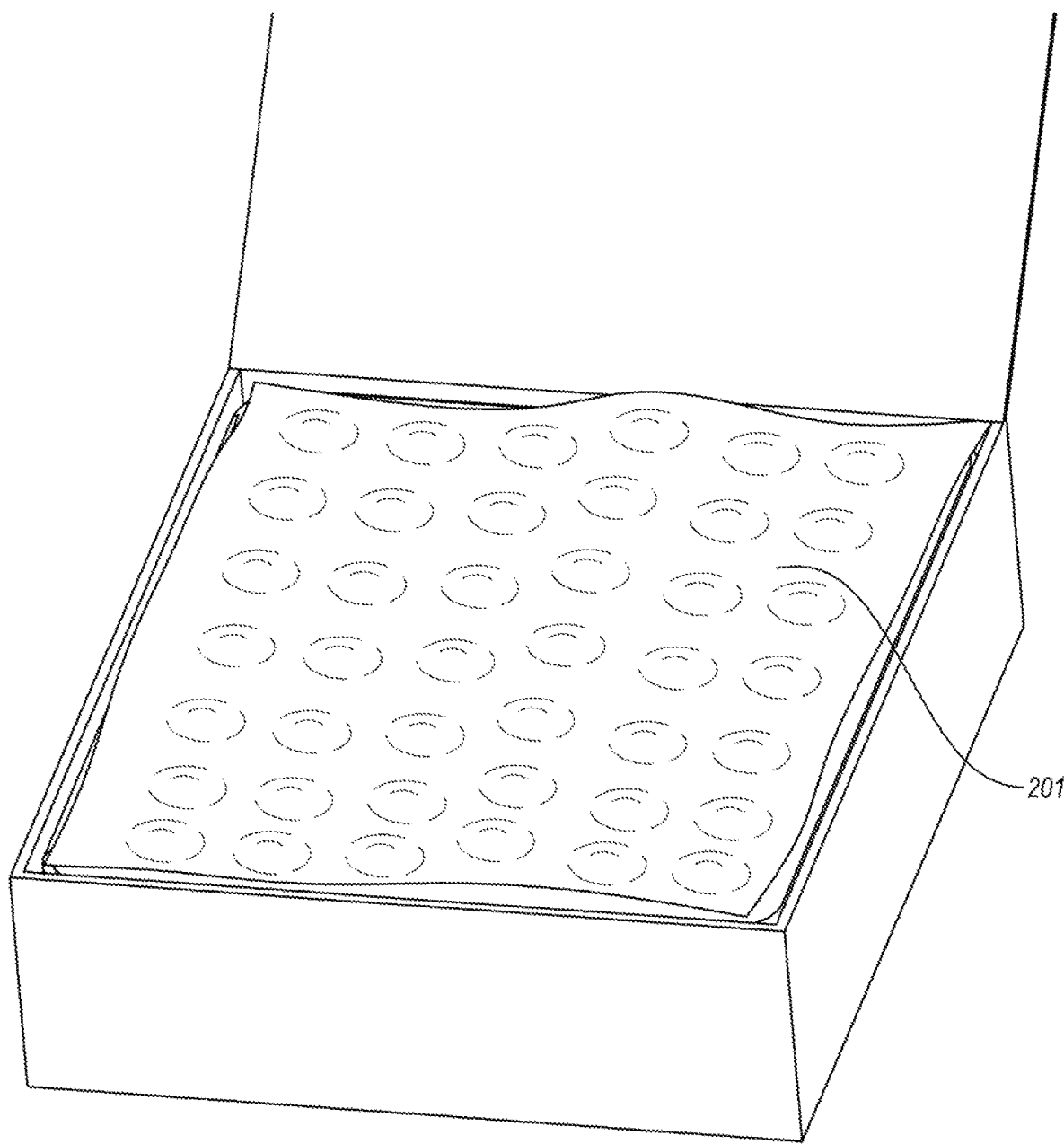
FIG. 18 illustrates the allergy testing kit in an open configuration according to FIG. 17.
Figure 19:
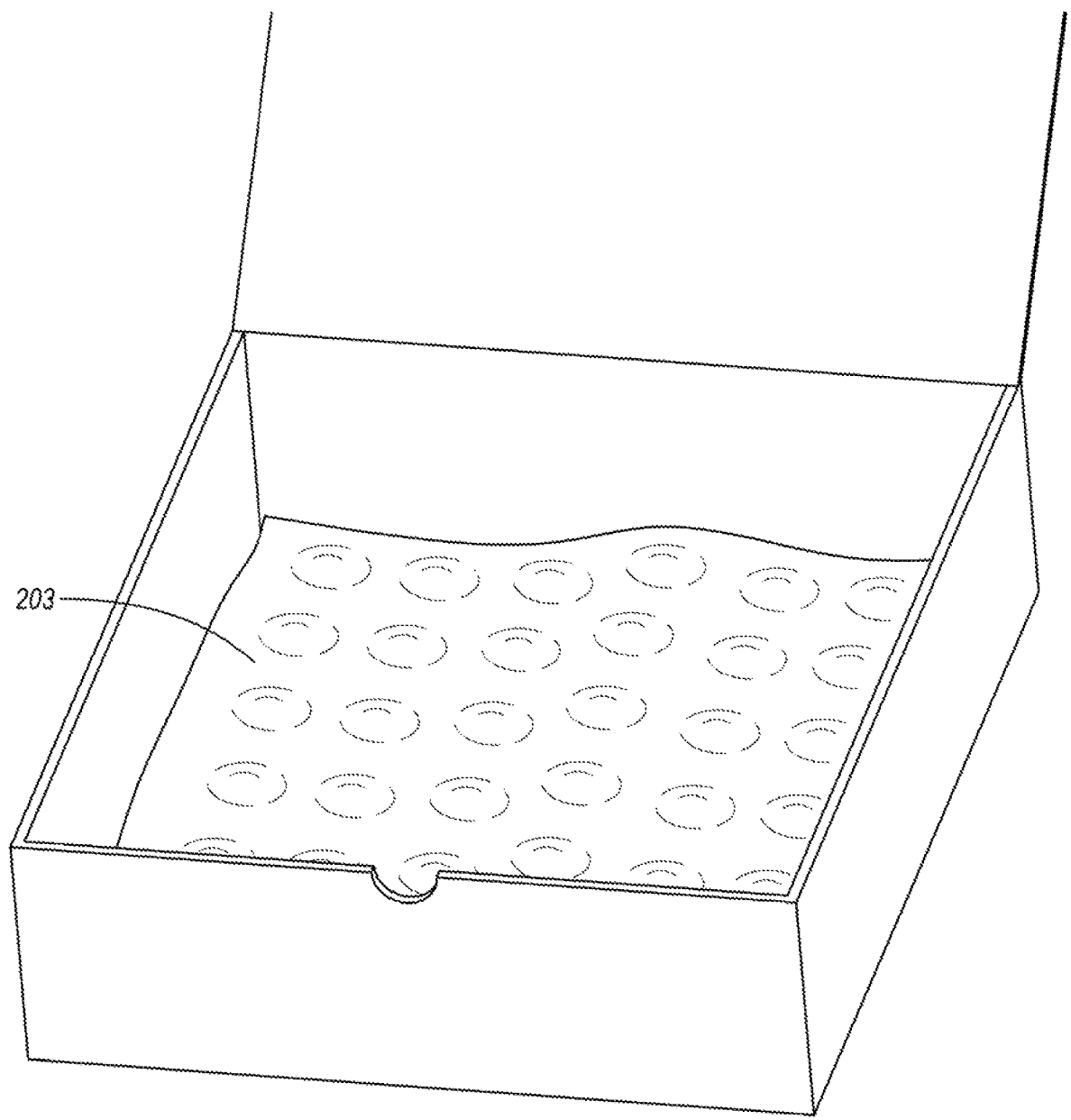
FIG. 19 illustrates the allergy testing kit packaging according to FIG. 17.
Figure 20:
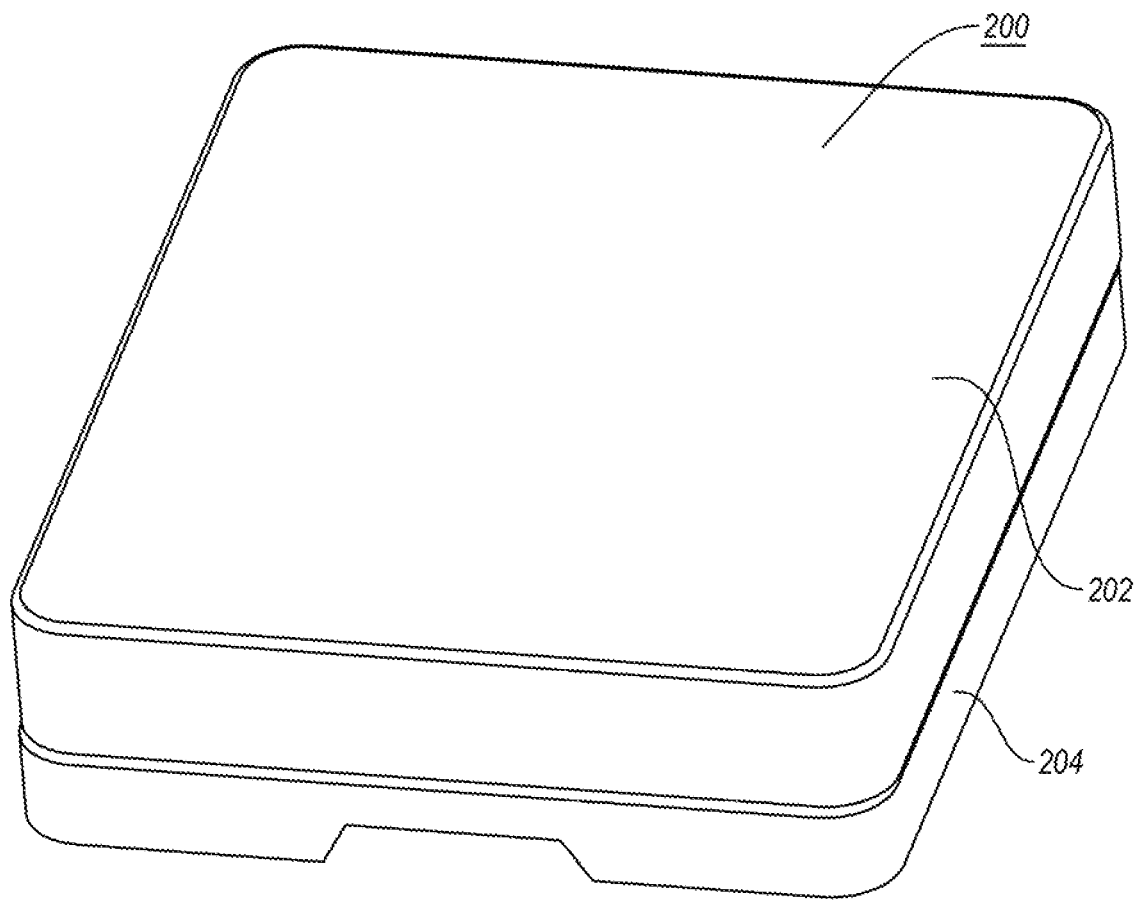
FIG. 20 illustrates the allergy testing kit according to FIG. 17.
Figure 21:
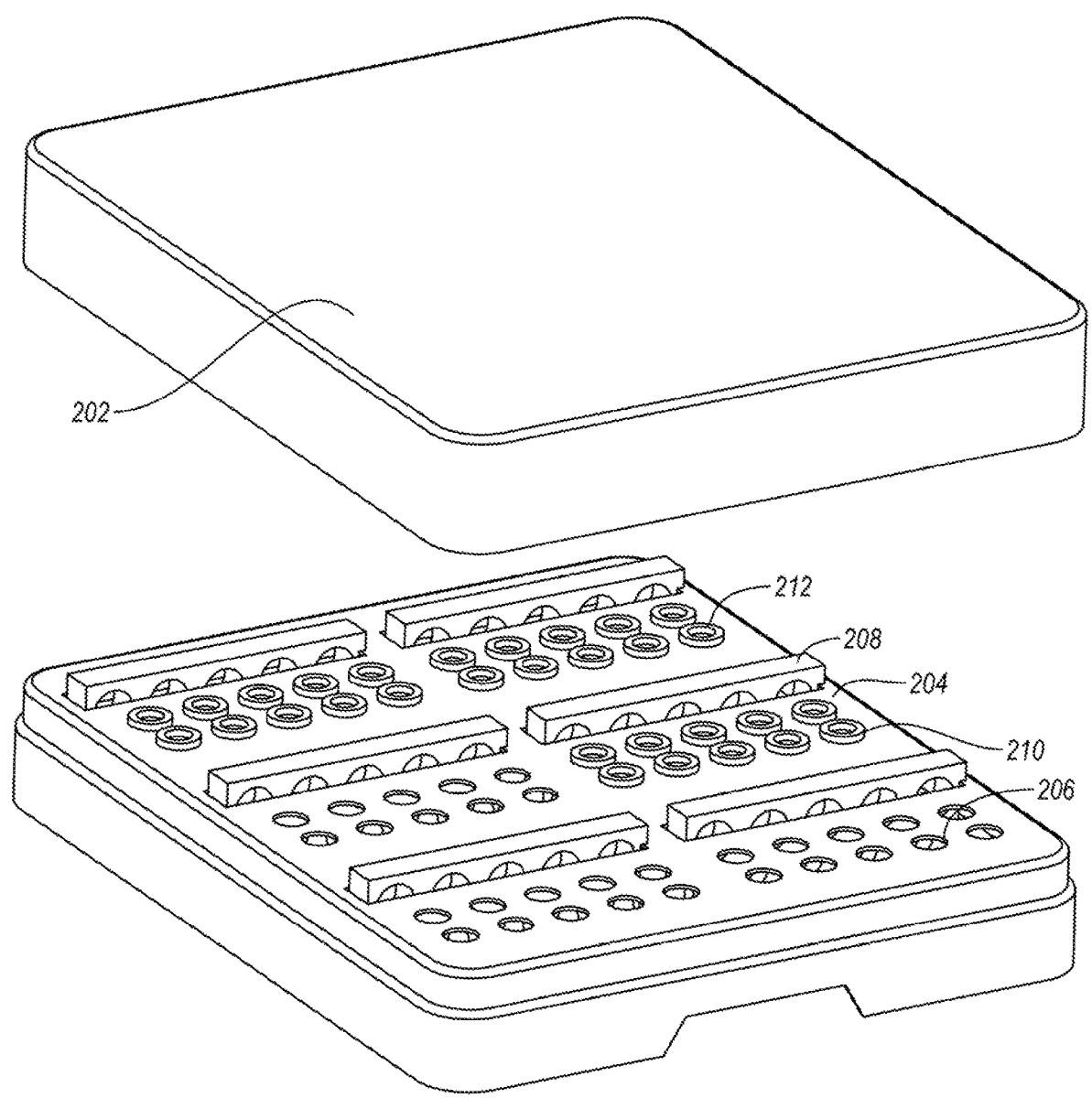
FIG. 21 illustrates the allergy testing kit according to FIG. 17.
Figure 22:
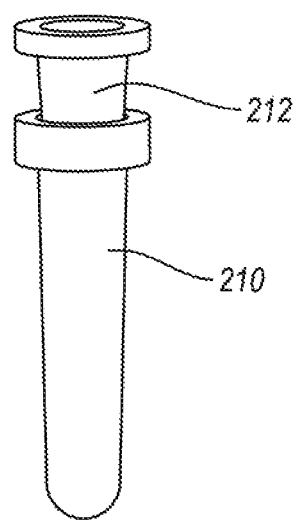
FIG. 22 illustrates a prefilled reservoir with a stopper or lid of the allergy testing kit according to FIG. 17.
Figure 23:
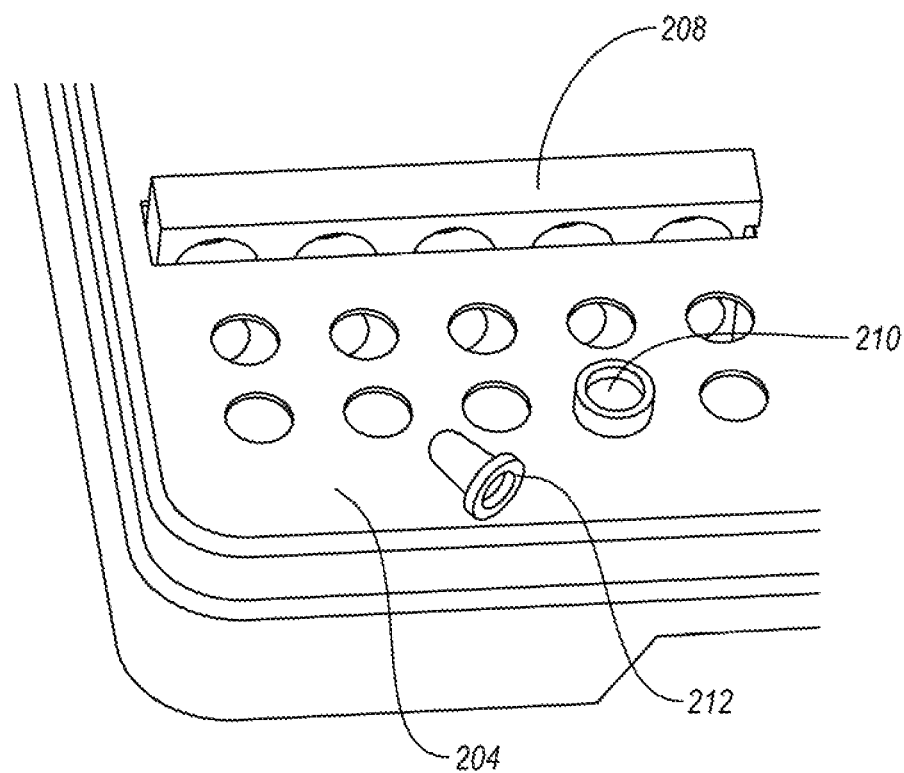
FIG. 23 illustrates a prefilled reservoir in a tray of the allergy testing kit according to FIG. 17.
Figure 24:
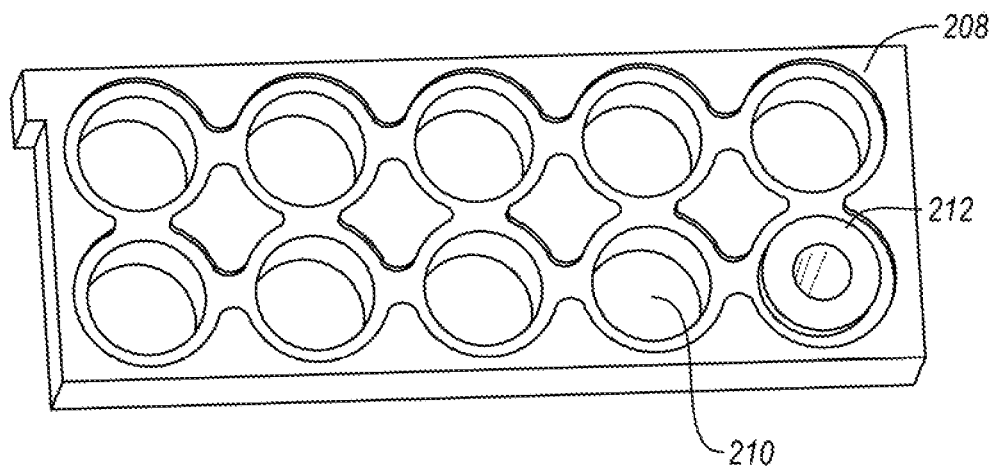
FIG. 24 illustrates a spacer and stopper of the allergy testing kit according to FIG. 17.
Figure 25:
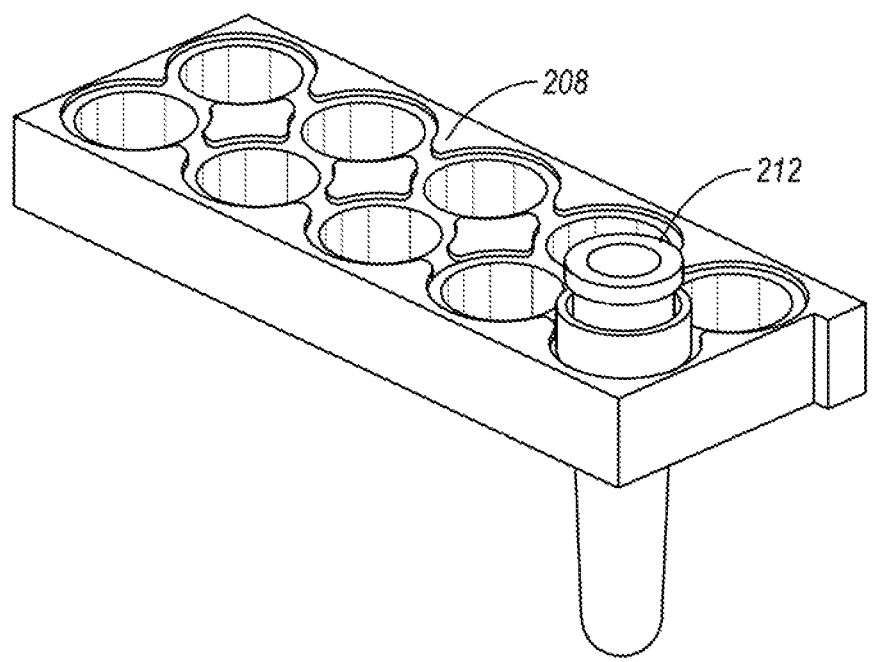
FIG. 25 illustrates a spacer and stopper of the allergy testing kit according to FIG. 17.
Figure 26:
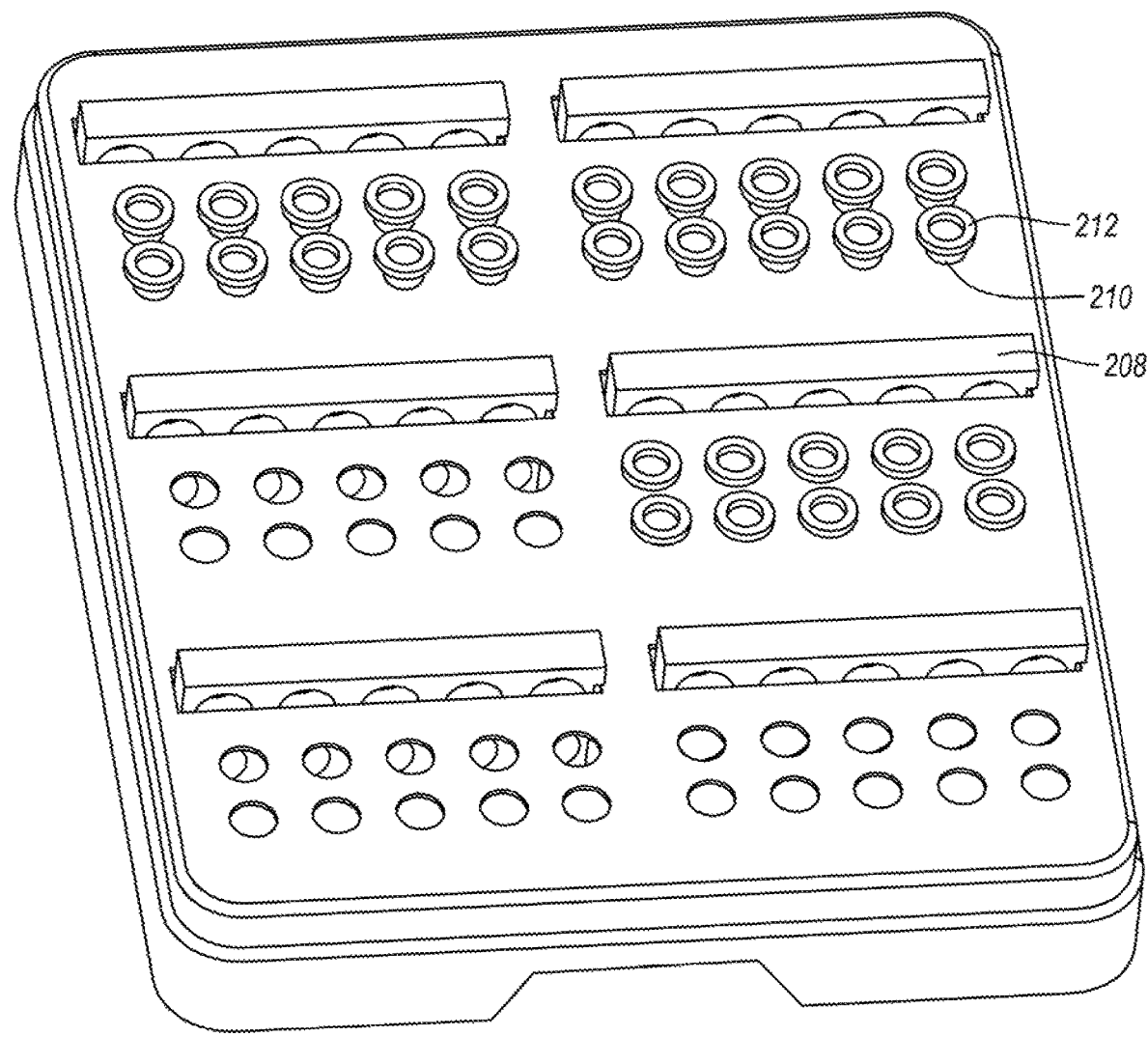
FIG. 26 illustrates the allergy testing kit according to FIG. 17.

FIG. 17 illustrating an allergy testing kit according to an embodiment of the invention. FIG. 18 illustrating the allergy testing kit in an open configuration according to FIG. 17. FIG. 19 illustrating the allergy testing kit packaging according to FIG. 17. FIG. 20 illustrating the allergy testing kit according to FIG. 17. FIG. 21 illustrating the allergy testing kit according to FIG. 17. FIG. 22 illustrating a prefilled reservoir of the allergy testing kit according to FIG. 17. FIG. 23 illustrating a prefilled reservoir in a tray of the allergy testing kit according to FIG. 17. FIG. 24 illustrating a spacer and stopper of the allergy testing kit according to FIG. 17. FIG. 25 illustrating a spacer and stopper of the allergy testing kit according to FIG. 17. FIG. 26 illustrating the allergy testing kit according to FIG. 17.

Referring to FIGS. 17-26, the allergy testing kit is generally depicted with reference to number 200. The allergy testing kit 200 is preconfigured to allow a clinician to rapidly perform allergy testing of patients with no mixing and minimal setup. The kit 200 includes two parts and an allergy testing kit 200 having the prefilled testing extracts to utilize with multiple patients, in a preferred embodiment twenty tests, and individual multiple skin test device kits each of which are used for single use with a single patient 250. In a preferred embodiment, twenty separate tests. The extracts are described above or known in the art.

The kit 200 includes a base region 204 and a removable top region 202 with a logo. Packaging 201 and 203 is used to protect the kit in shipping, for example, bubble wrap, foam, and/or combinations of the same. Optionally and/or alternatively, the packing may include insulated or refrigerated packaging. The base 204 includes plurality of holes 206 configured to receive and securely hold prefilled reservoirs 210 in a grid pattern. The grid pattern matches the lancets of the multiple skin test device for puncturing skin testing. Each of the prefilled reservoirs are removably attached to the base 202 via holes 206. The prefilled reservoirs 210 are filed with allergen extracts used in testing a patient's immune response. In one embodiment, the base is from HollisterStier Allergy® and is a ComforTen® Covered 60-Hole which is 11 inches by nine and half inches by three and one eight inches with six spacers and holds 60 HollisterStier Allergy Skin Test Reservoirs. The spacers are described with reference to U.S. Design Pat. No. D596758, which is hereby incorporated by reference.

The selection and number of allergen extracts is predetermined and based on the geographic region of the end patient and treatment desires of the patient and/or clinician. The kit 200 is highly customizable and can be used with more than one patient. In a preferred embodiment, each of the multiple skin test device kits 250 include six skin test device for puncture skin testing, e.g., ComforTen® by HollisterStier. The skin test lancets are used with the extracts to test a patient by receiving administering the selected extract to a patient.

In a preferred embodiment, the kit 200 includes ninety prefilled reservoirs arranged securely in the kit 200 with allergen extracts. It is noted that kit may include 180 extracts or less to test the patient. Each of the reservoirs 210 are about 1 cc and configured to receive about 0.6 cc of extract. A stopper or lid 212 is used to prevent or substantially prevent spillage of the extracts during shipping and/or handling. In a preferred embodiment, the reservoirs 210 contain one or more allergens to test on an end patient, each skin test reservoir including a stopper or lid 212 securely arranged in at least a portion of the reservoir. In a preferred embodiment, the stopper or lid 212 includes a thermoplastic material that is malleable to aid in insertion into the reservoir 210. The base 204 also includes slots to hold a spacer 208. The spacer 208 is described with reference to U.S. Design Pat. No. D596758, which is hereby incorporated by reference. Optionally and/or alternatively, the base includes regions 204 to label each prefilled reservoir with information indicative of the extract.

The spacer 208 and the stopper are used during shipping in order to allow more extract to be shipped with each kit 200. In a preferred embodiment, there are 30 prefilled reservoirs in segments of 10. Six spacers 208 are used to cover each of the 10 reservoirs 210 as shown in FIG. 24 in order of reservoir 210, spacer 208, and stopper 212. This configuration allows about 0.6 cc or more of extract to be shipped in order to prevent a first end of the stopper 212 from displacing prefilled extract in the reservoir. In this configuration less extract must be used as there would be more displacement.

In a preferred embodiment, there are 30 prefilled reservoirs in segments of 10. Six spacers 208 are used to cover each of the 10 reservoirs 210 as shown in FIG. 24 in order of reservoir 210, spacer 208, and stopper 212. This configuration allows about 0.6 cc or more of extract to be shipped in order to prevent a first end of the stopper 212 from displacing prefilled extract in the reservoir. In this configuration less extract must be used as there would be more displacement.

After the kit is received the stoppers 212 are removed and can be tested with the skin test devices by dipping the skin test devices into the reservoirs with or without the spacers 208 to receive the prefilled extracts. Puncture the skin and wait a predetermined amount of time for a reaction, e.g., 5 minutes or greater. Circle the top five reactions with the pen 270 and record size of reaction with ruler. Correlate extract to the reaction and input or provide to provider to determine treatment recommendation.

Figure 27:
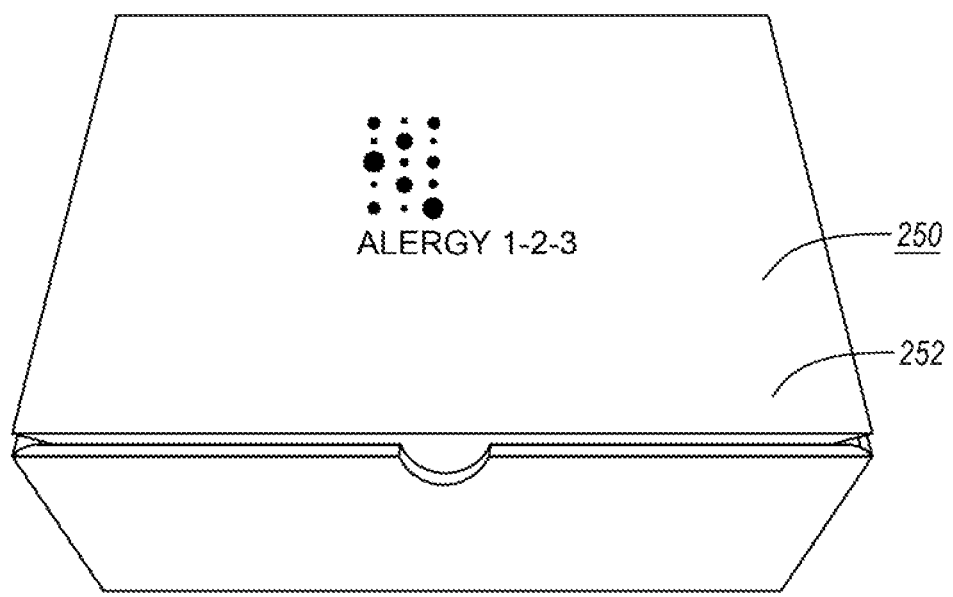
FIG. 27 illustrates a multiple skin test package for puncturing skin of the allergy testing kit.
Figure 28:
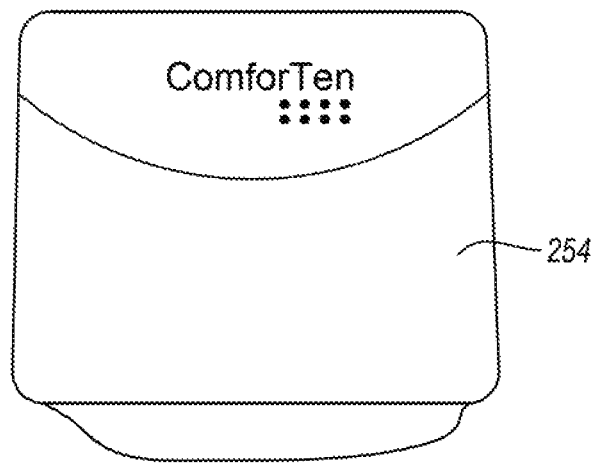
FIG. 28 illustrates a multiple skin test device for puncturing skin testing of the allergy testing kit.
Figure 29:
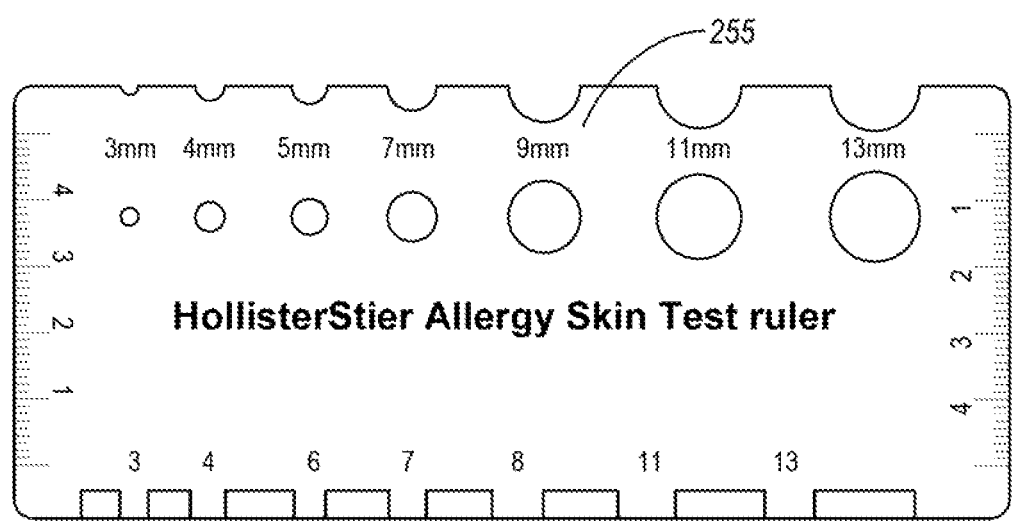
FIG. 29 illustrates an allergy skin test ruler of the allergy testing kit.
Figure 30:
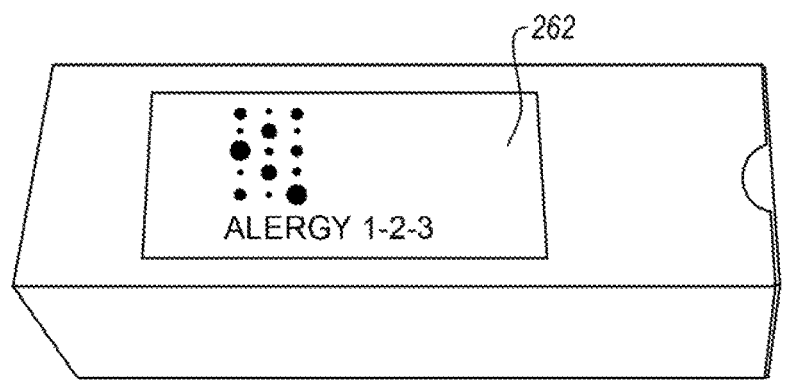
FIG. 30 illustrates an individual patient treatment package of the allergy testing kit.
Figure 31:
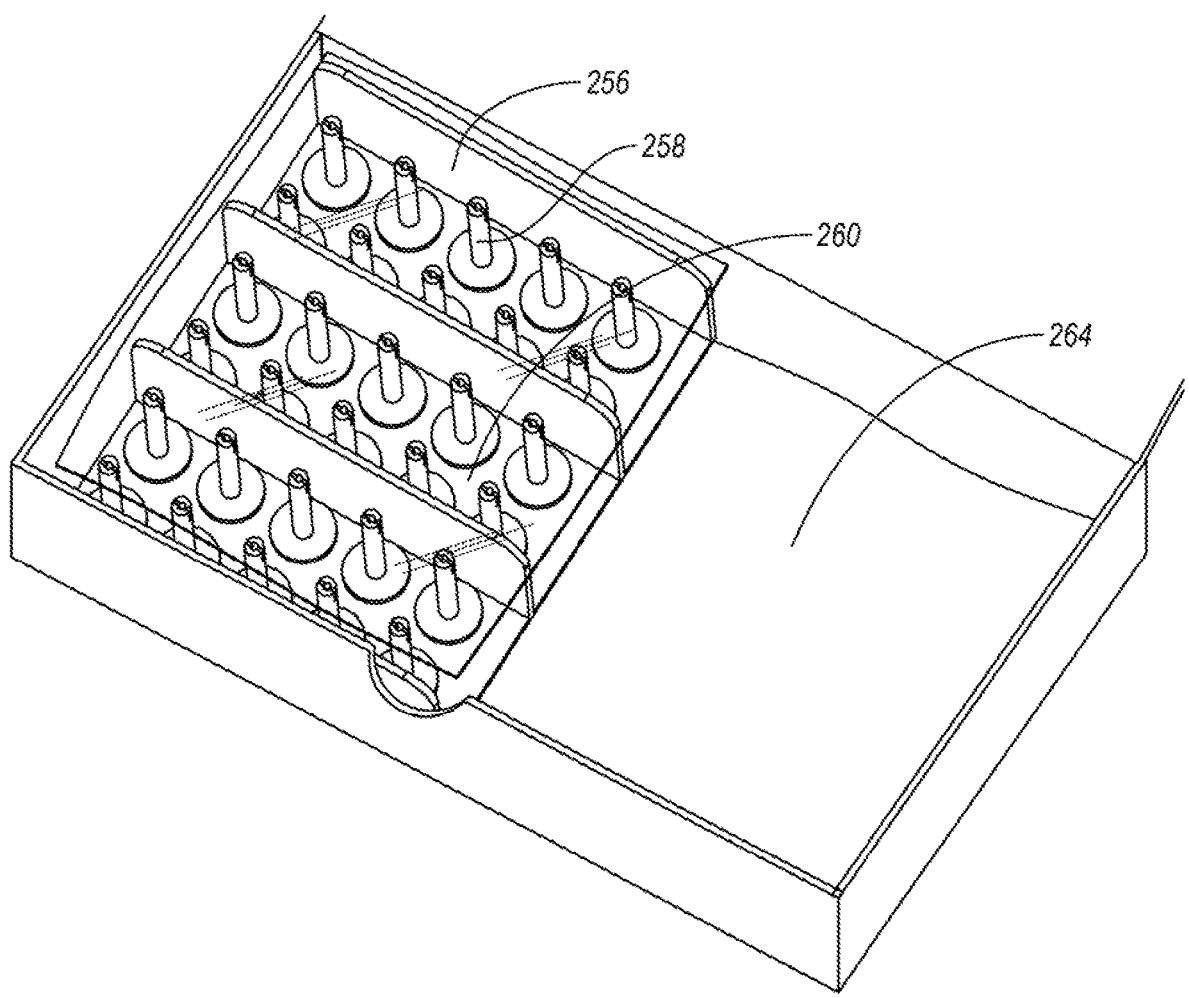
FIG. 31 illustrates a multiple skin test device for puncturing skin testing of the allergy testing kit.
Figure 32:
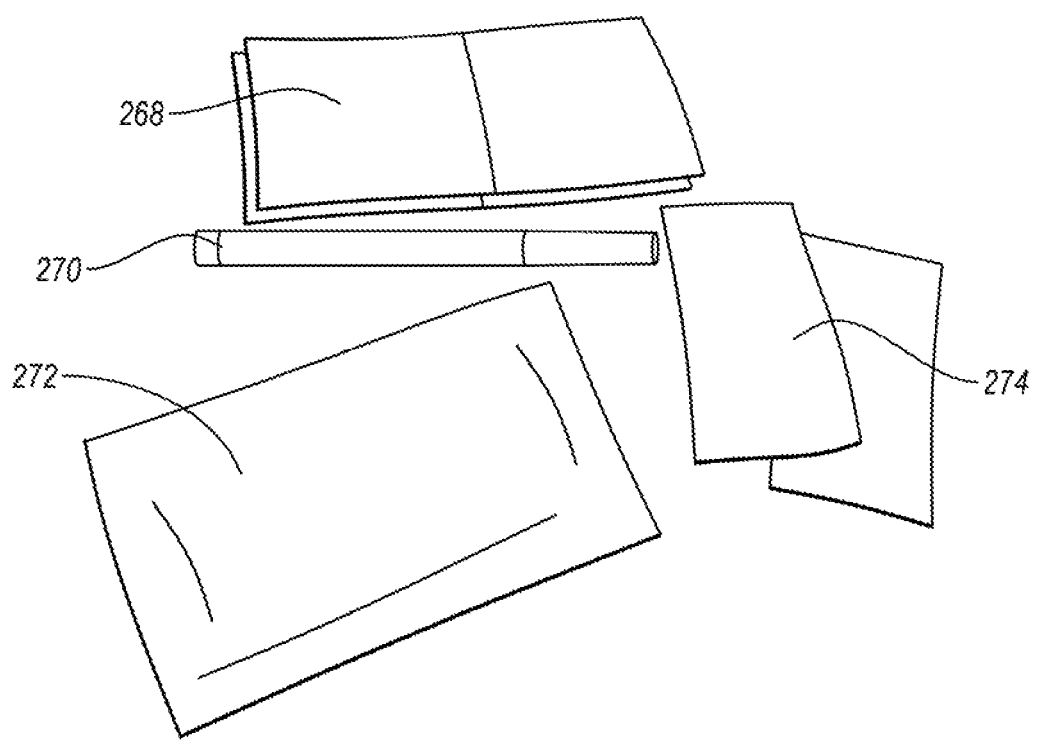
FIG. 32 illustrates the components of individual patient treatment package of the allergy testing kit.

FIG. 27 illustrating a multiple skin test device for puncturing skin of the allergy testing kit. FIG. 28 illustrating a multiple skin test device for puncturing skin testing of the allergy testing kit. FIG. 29 illustrating an allergy skin test ruler of the allergy testing kit. FIG. 30 illustrating an individual patient treatment package of the allergy testing kit. FIG. 31 illustrating a multiple skin test device for puncturing skin testing of the allergy testing kit. FIG. 32 illustrating the components of individual patient treatment package of the allergy testing kit of FIG. 30.

Referring to FIGS. 27-32, the multiple skin test device kit 250 for puncturing skin of the allergy testing kit is depicted. The kit 250 is an individual patient test kit configured for single use and ease of clinician use. The kit 250 includes a container 252, two HollisterStier ComforTen® multiple skin test devices 254 for puncturing skin testing devices each including three separate test units a first unit 256, a second unit 258 and a third unit 260 for a total of thirty puncture for each test device 254 or sixty total lancets for two test devices 254 for puncturing skin as shown in FIG. 31. Other types of multiple skin test devices may be utilized. The kit further includes one or more sterile towels 264 and an allergy skin test ruler 255 are also included in the kit 250. The kit 250 further includes a patient unit container 262 including alcohol wipes 268, surgical marker 270, wet ones 272, anti-inflammatory ointment 274. The number and arrangement of containers configured with the kits is done to simplify and organize the components. Optionally and/or alternatively a thermoform may be used to hold each or predetermined components of the kit 250.

Figure 33:
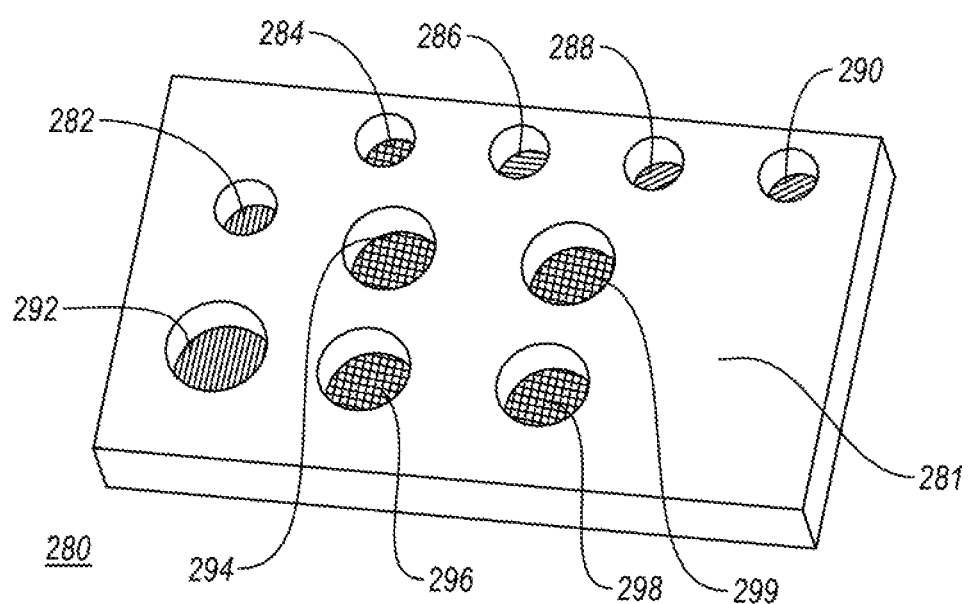
FIG. 33 illustrates a top-down view of a mixing tray according to another embodiment of the invention.

FIG. 33 illustrates a top-down view of a mixing tray of the immunotherapy treatment kit or mixing kit according to an embodiment of the invention.

Referring to FIG. 33, the mixing tray is generally depicted with reference to number 280. The mixing try 280 includes a plurality of color coded slots configured to receive vials of the patient test kit herein. The mixing try 280 includes a red color coded slot 282 sized to receive a 5 cc empty concentrate vial 130, a yellow color coded slot 284 sized to receive a 5 cc vial having a label indicative of a 1:5 concentrate vial 152 prefilled with 4.0 cc of ABS dilute, a blue color coded slot 286 sized to receive a 5 cc vial having a label indicative of a 1:50 concentrate vial 148 prefilled with 4.5 cc of ABS dilute, a green color coded slot 288 sized to receive a 5 cc vial having a label indicative of a 1:500 concentrate vial 146 prefilled with 4.5 cc of ABS dilute, a silver color coded slot 290 sized to receive a 5 cc vial having a label indicative of a 1:5000 concentrate vial 142 prefilled with 4.5 cc of ABS dilute, a yellow color coded slot 294 sized to receive a 10 [cc] vial having a label indicative of a 1:5 concentrate vial 154 prefilled with 8.0 [cc] of ABS dilute, a yellow color coded slot 296 sized to receive a 10 cc vial having a label indicative of a 1:5 concentrate vial 156 prefilled with 8.0 [cc] of ABS dilute, a red color coded slot 292 sized to receive a 10 [cc] vial having a label indicative of a concentrate vial, a yellow color coded slot 299 sized to receive a 10 [cc] vial having a label indicative of a 1:5 concentrate vial prefilled with ABS dilute, a yellow color coded slot 298 sized to receive a 10 [cc] vial having a label indicative of a 1:5 concentrate vial prefilled with ABS dilute, and a logo region 281.

One embodiment is directed towards a method of using the kits described herein.

One embodiment is directed towards a method using the mixing kit 100 and the mixing tray described herein above. In this embodiment, the kit 100 and the mixing tray 280 arrive at the provider's office, e.g., by a postal service. The kit 100 includes a preconfigured custom patient immunotherapy system for making a one year homebased immunotherapy for a patient. The provider uses the kit to make a one year immunotherapy. Optionally and/or alternatively the kit can be configured for treating one or more allergen for three months or more time, e.g., one year or greater.

In this embodiment, the kit 100 is configured to provide a custom one year immunotherapy treatment. This is used by a provider to mix a custom one year five allergen treatment to a patient. The kit 100 includes five custom extracts, a first prefilled 1 [cc] syringe 116 containing a first extract treatment, a second 1 [cc] syringe 118 containing a second extract treatment, a third 1 [cc] syringe 120 containing a third extract treatment, a fourth 1 [cc] syringe 122 containing a forth extract treatment, and a fifth 1 [cc] syringe 114 containing a fifth extract treatment. In this embodiment, the syringes 116, 118, 120, 122, and 114 are prefilled with 1 [cc] of preselected extracts. In one embodiment, the extracts are selected by a provider based on test results of a patient from application of a testing kit described herein. Optionally and/or alternatively the selection of extracts by a provider is either done or supplemented with an aid of electronic device configured to programically deduce a treatment recommendation as described with reference to U.S. Patent Application Publication No. 2016/0026765, which is hereby incorporated by reference as if fully set forth herein.

Optionally and/or alternatively, a provider can use a custom mixing tray (as described with reference to FIG. 33 to assist the provider with mixing the custom immunotherapy. In one embodiment, a mixing tray is not utilized. In this embodiment, the provider uses a mixing tray provided with the kit 100 or separately. The provider does an initial setup of the mixing try by adding the empty red concentrate vial 130 to the red color coded slot 282, the yellow concentrate vial 152 is placed in the yellow color coded slot 284, the blue concentrate vial 148 is placed in the blue color coded slot 286, the green concentrate vial 146 is placed in the green color coded slot 288, the silver vial 142 is placed is placed in the silver color coded slot 290, the yellow concentrate vial 154 is placed in the yellow color coded slot 294, and the yellow concentrate vial 156 is placed in the yellow color coded slot 296.

In this embodiment, the red concentrate vial 130 is shipped empty, the yellow concentrate vial 152 is prefilled with 4.0 [cc] ABS, the blue concentrate vial 148 is prefilled with 4.5 [cc] ABS, the green concentrate vial 146 is prefilled with 4.5 [cc] ABS, the silver concentrate vial 142 is prefilled with 4.5 [cc] ABS, the yellow concentrate vial 154 is prefilled with 8.0 [cc] ABS, and the yellow concentrate vial 156 is prefilled with 8.0 [cc] ABS. Optionally and/or alternatively, the kit 100 may be shipped premixed with extracts to a desired concentration.

The luer-lock tops 164 on the syringes 116, 118, 120, 122, and 114. Next, the provider will add needles to each syringe 116, 118, 120, 122, and 114. Next, the provider will completely empty the contents of each syringe into the red concentrate vial 130 is placed in the mixing tray at slot 282, the yellow concentrate vial 152 is placed in the color coded slot 284, the blue concentrate vial 148 is placed in the blue color coded slot 286, the green concentrate vial 146 is placed in the color coded slot 288, the silver vial 142 is placed in the color coded slot 290, the yellow concentrate vial 154 is placed in the color coded slot 294, and the yellow concentrate vial 156 is placed in the color coded slot 296.

Next, a clinician empties the contents of syringes 116, 118, 120, 122, and 114 into the red concentrate vial 130 and slightly swirls the new concentrate mix, the mixed concentrate now containing five concentrated antigens. That is, the concentrate mix now contains the custom allergen contents of each the syringes 116, 118, 120, 122, and 114 received in the mail. In a preferred embodiment, the syringes will include five separate custom allergen extracts used to create a year supply of immunotherapy for the patient. The therapy will include a six months of increased concentrations, e.g., a linear or non-linear ramp of increased dosages and maintenance dosages having a constant concentration. In a preferred embodiment, the concentration ramp includes 1:5000 (silver), 1:500 (blue), 1:50 (green) and 1:5 (yellow). The ratio is allergen extract to ABS diluent.

Next, a clinician removes with a 1 [cc] syringe a volume of 1 [cc] from the red concentrate vial 130 now containing a 5 [cc] concentrate allergen mix. The removed 1 [cc] is added to the yellow vial 152 which is prefilled with 4.0 [cc] of ABS diluent, thereby creating 5.0 [cc]. Next, 0.5 [cc] is removed from vial 152 with a syringe and added to the blue vial 148 containing 4.5 [cc] of ABS diluent. Next, 0.5 [cc] is removed from vial 148 with a syringe and added to the green vial 146 containing 4.5 [cc] of ABS diluent. Next, 0.5 [cc] is removed from vial 146 with a syringe and added to the silver vial 142 containing 4.5 [cc] of ABS diluent.

At this point, the yellow vial 152 now contains 4.5 [cc] of concentrate at a ratio of 1:5, the blue vial 148 now contains 4.5 [cc] of concentrate at a ratio of 1:50, the green vial 146 now contains 4.5 [cc] of concentrate at a ratio of 1:500, and the silver vial 142 now contains 4.5 [cc] of concentrate at a ratio of 1:5000.

Next, a clinician removes with a syringe a volume of 2 [cc] from the red concentrate vial 130 now containing a 4 [cc] concentrate allergen mix and adds the 2 [cc] to the yellow vial 154 containing 8.0 [cc] of ABS diluent. Next, a clinician removes with a syringe a volume of 2 [cc] from the red concentrate vial 130 now containing a 2 [cc] concentrate allergen mix and adds the 2 [cc] to the yellow vial 156 containing 8.0 [cc] of ABS diluent. The mixing of the one year immunotherapy is now complete. The mix includes a ramp treatment and a maintenance treatment. The ramp treatment includes vials 152, 148, 146, and 142, which is used over a ramp time of the treatment. The maintenance treatment includes vials 152, 148, 146, and 142, which is used over a maintenance time of the treatment. In a preferred embodiment, a patient conducts immunotherapy in a home-based maintenance treatment over 6 months and ramp treatment over 6 months. Optionally and/or alternatively a treatment by a patient can be conducted as described with reference U.S. Pat. Application Publication No. 2016/0026765 and U.S. Pat. Application Publication No. 2016/0022539, each of which are hereby incorporated by reference. The treatment can be conducted with an injector pen as described with reference U.S. Patent Application Publication No. 2016/0022539, which is hereby incorporated by reference.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this description, with each claim standing on its own as a separate preferred embodiment of the disclosure.

Moreover, though the description has included a description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for mixing a custom allergy treatment for use by a clinician based on a specific immune response of a patient and configured to treat the patient for allergies with a custom allergy mixing kit, comprising the steps of:

receiving the custom allergy mixing kit, the custom allergy mixing kit comprising a container, the container comprising an allergy patient packet, a sterile napkin, a patient prescription package, a clinic prescription package, and a first prefilled container with a first allergen extract based on a first specific immune response of the patient, a second prefilled container with a second allergen extract based on a second specific immune response of the patient, a third prefilled container with a third allergen extract based on a third specific immune response of the patient, a fourth prefilled container with a fourth allergen extract based on a fourth specific immune response of the patient, and a fifth prefilled container with a fifth allergen extract based on a fifth specific immune response of the patient, wherein the patient prescription package comprises an empty sterile vial with a color code indicative of a concentrate concentration, one or more needles, one or more rubber bands, and one or more alcohol wipes, wherein the clinic prescription package comprises a first vial comprising a color code indicative of 1:5000 concentration, the first vial is prefilled with a first predetermined volume of albumin buffered saline (ABS) dilute, a second vial comprising a color code indicative of 1:500 concentration, the second vial is prefilled with a second predetermined volume of albumin buffered saline (ABS) dilute, a third vial comprising a color code indicative of 1:50 concentration, the third vial is prefilled with a third predetermined volume of albumin buffered saline (ABS) dilute, a fourth vial comprising a color code indicative of 1:5 concentration, the fourth vial is prefilled with a fourth predetermined volume of albumin buffered saline (ABS) dilute, a fifth vial comprising a color code indicative of 1:5 concentration, the fifth vial is prefilled with a fifth predetermined volume of albumin buffered saline (ABS) dilute, and a sixth vial comprising a color code indicative of 1:5 concentration, the sixth vial is prefilled with a sixth predetermined volume of albumin buffered saline (ABS) dilute, wherein the fourth predetermined volume is different than the first predetermined volume; and filling the empty vial with contents of the first prefilled container, the second prefilled container, the third prefilled container, the fourth prefilled container, and the fifth prefilled container to form a custom allergen concentrate mix.

2. The method of claim 1, wherein the allergy patient packet comprises instructions for use of the patient prescription package.

3. The method of claim 1, wherein the custom allergy mixing kit further comprises a mixing tray.

4. The method of claim 3, wherein the mixing tray comprises one or more color codes indicative of a concentration of a desired allergen extract mix.

5. The method of claim 3, further comprising holding one or more of the first vial, the second vial, the third vial, the fourth vial, the fifth vial, and the sixth vial using the mixing tray.

6. The method of claim 1, further comprising the steps of adding a predetermined volume of the custom allergen concentrate mix to the sixth vial that is prefilled with the sixth predetermined volume of albumin buffered saline (ABS) dilute to form a 1:5 concentration of the custom allergy treatment.

7. The method of claim 6, further comprising the steps of placing the first vial with a 1:5000 concentration of the allergen concentrate mix in the patient prescription package.

8. The method of claim 6, further comprising the steps of adding a seventh predetermined volume of the sixth vial to the second vial prefilled with the second predetermined volume of albumin buffered saline (ABS) dilute to form a 1:500 concentration of the custom allergy treatment.

9. The method of claim 8, further comprising the steps of adding an eighth predetermined volume of the second vial to the third vial prefilled with the third predetermined volume of albumin buffered saline (ABS) dilute to form a 1:50 concentration of the custom allergy treatment.

10. The method of claim 8, further comprising the steps of adding a ninth predetermined volume of the third vial to the first vial prefilled with the first predetermined volume of albumin buffered saline (ABS) dilute to form a 1:5000 concentration of the custom allergy treatment.

11. The method of claim 1, wherein the first prefilled container with the first allergen extract comprises a first syringe, the second prefilled container with the second allergen extract comprises a second syringe, the third prefilled container with the third allergen extract comprises a third syringe, the fourth prefilled container with the fourth allergen extract comprises the fourth syringe, the fifth prefilled container with the fifth allergen extract comprises a fifth syringe.

12. The method of claim 1, further comprising the steps of:
using the allergen concentrate mix with the first vial, the second vial, the third vial, the fourth vial, the fifth vial, and the sixth vial of the clinic prescription package to form the custom allergy treatment.

13. The method of claim 12, wherein the custom allergy treatment comprises the first vial comprising a custom allergy treatment having a 1:5000 concentration of the allergen concentrate mix, the second vial comprising a custom allergy treatment having a 1:500 concentration of the allergen concentrate mix, the third vial comprising a custom allergy treatment having a 1:50 concentration of the allergen concentrate mix, the fourth vial comprising a custom allergy treatment having a 1:5 concentration of the allergen concentrate mix, the fifth vial comprising a custom allergy treatment having a 1:5 concentration of the allergen concentrate mix, and the sixth vial comprising a custom allergy treatment having a 1:5 concentration of the allergen concentrate mix.

* * * * *